(12) United States Patent
Church et al.

(10) Patent No.: US 9,624,538 B2
(45) Date of Patent: Apr. 18, 2017

(54) NANOGRID ROLLING CIRCLE DNA SEQUENCING

(75) Inventors: George M. Church, Brookline, MA (US); Gregory J. Porreca, Ocean City, NJ (US); Jay Shendure, Chagrin Fall, OH (US); Abraham Meir Rosenbaum, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 171 days.

(21) Appl. No.: 12/120,541

(22) Filed: May 14, 2008

(65) Prior Publication Data
US 2009/0018024 A1 Jan. 15, 2009

Related U.S. Application Data

(63) Continuation of application No. PCT/US2006/044209, filed on Nov. 14, 2006.

(60) Provisional application No. 60/736,923, filed on Nov. 14, 2005.

(51) Int. Cl.
C12Q 1/68 (2006.01)

(52) U.S. Cl.
CPC ............................ *C12Q 1/6874* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,210,015 | A | 5/1993 | Gelfand et al. |
| 5,399,491 | A | 3/1995 | Kacian et al. |
| 5,854,033 | A | 12/1998 | Lizardi |
| 6,174,670 | B1 | 1/2001 | Wittwer et al. |
| 6,432,360 | B1 | 8/2002 | Church |
| 6,485,944 | B1 | 11/2002 | Church et al. |
| 6,511,803 | B1 | 1/2003 | Church et al. |
| 7,785,790 | B1 | 8/2010 | Church et al. |
| 7,960,104 | B2 | 6/2011 | Drmanac et al. |
| 8,133,719 | B2 | 3/2012 | Drmanac et al. |
| 2002/0012930 | A1* | 1/2002 | Rothberg et al. ............ 435/6 |
| 2006/0173628 | A1* | 8/2006 | Sampas .................. G06K 9/32 702/19 |
| 2007/0099208 | A1* | 5/2007 | Drmanac et al. ............ 435/6 |

FOREIGN PATENT DOCUMENTS

JP          4-262799          9/1992

OTHER PUBLICATIONS

Mirta (Jul. 15, 2003) Analytical Biochemistry vol. 320 p. 55.*
Cutler (Oct. 15, 2001) Genome Research vol. 11 pp. 1913 to 1925.*
Mirta (Jul. 15, 2003) Analytical Biochemistry vol. 320 pp. 55 to 65.*
Shendure (May 2004) Nature Reviews Genetics vol. 5 pp. 335 to 344.*
An et al., "Characterization of a Thermmostable UvrD Helicase and its Participation in Helicase-Dependent Amplification," *J. Biol. Chem.* 280(32):28952 (2005).
Blanco et al., "Highly Efficient DNA Synthesis by the Phage ø29 DNA Poylmerase," *J. Biological Chemistry* (1989).
Bulyk et al., "Exploring the DNA-binding specificities of zinc fingers with DNA microarrays," *PNAS*, 98(13):7158-7163 (2001).
Dahl et al., "Circle-to-circle amplification for precise and sensitive DNA analysis," *Proc. Natl. Acad. Sci. U.S.A.*, 101(13):4548-4553 (2004).
Demidov, "New kids on the block: emerging PNA-based DNA diagnostics," *Expert Rev. Mol. Diagn.* 2(3):89-91 (2002).
Demidov, "Rolling-circle amplification in DNA diagnostics: the power of simplicity," *Expert Rev. Mol. Diagn.* 2(6):89-91 (2002).
Ge et al. (2005) *Nano. Lett.* 5(1):179.
Jung et al., "Vapor-Phase Self-Assembled Monolayer for Improved Mold Release in Nanoimprint Lithography," *Langmuir* 21(4):1158-1161 (2005).
Jung et al., "Improved Pattern Transfer in Nanoimprint Lithography at 30 nm Half-Pitch by Substrate-Surface Functionalization," *Langmuir* 21(14):6127-6130 (2005).
Kwok, "High-throughput genotyping assay approaches," *Pharmiocogenomics* 1:95-100 (2000).
Landegren et al., "A Ligase-Mediated Gene Detection Technique," *Science*, 241:1077-1080 (1988).
Lenhert et al., "Osteoblast alignment, elongation and migration on grooved polystyrene surfaces patterned by Langmuir-Blodgett lithography," *Biomaterials* 26(5):563-570 (2005).
Liang et al., "Electrostatic Force-Assisted Nanoimprint Lithography," *Nano Lett.* 5(3):527-530 (2005).
Lizardi et al., "Mutation detection and single-molecule counting using isothermal rolling-circle amplification," *Nat. Genet.*, 19:225-229 (1998).
Luesebrink et al., "Transition of MEMS Technology to Nanofabrication," *J. Nanosci. Nanotechnol.* 5(6):864-868 (2005).
Nilsson et al., "Padlock Probes: Circularizing Oligonucleotides for Localized DNA Detection," *Science*, 265(5181):2085-2087 (1994).
Schweitzer et al., "Multiplexed protein profiling on microarrays by rolling-circle amplification," *Nat. Biotech.*, 20:359-365 (2002).
Shi, "Enabling Large-Scale Pharmacogenetic Studies by High-Throughput Mutation Detection and Genotyping Technologies," *Clin. Chem.*, 47:164-172 (2001).
Yan et al., "Fabrication of Large Number Density Platinum Nanowire Arrays by Size Reduction Lithography and Nanoimprint Lithography," *Nano. Lett.*, 5(4):745-748 (2005).
Yim et al., "Nanopattern-induced changes in morphology and motility of smooth muscle cells," *Biomaterials*, 26(26):5405-5413 (2005).

* cited by examiner

*Primary Examiner* — Aaron Priest
(74) *Attorney, Agent, or Firm* — Banner & Witcoff, Ltd.

(57) ABSTRACT

The present invention relates to methods for sequencing a polynucleotide immobilized on an array having a plurality of specific regions each having a defined diameter size, including synthesizing a concatemer of a polynucleotide by rolling circle amplification, wherein the concatemer has a cross-sectional diameter greater than the diameter of a specific region, immobilizing the concatemer to the specific region to make an immobilized concatemer, and sequencing the immobilized concatemer.

19 Claims, 14 Drawing Sheets
(10 of 14 Drawing Sheet(s) Filed in Color)

SBL of Synthetic Library

SBL -1 Possible Bases: A, T

Blue: Universal Primer
Red: Cy5-T
Green: Cy3-A

SBL -5 Possible Bases: A, T, G, C

Blue: Universal Primer
Red: Cy5-T
Green: Cy3-A

US 9,624,538 B2

NANOGRID ROLLING CIRCLE DNA SEQUENCING

RELATED U.S. APPLICATIONS

This application is a continuation of PCT application no. PCT/US2006/044209, designating the United States and filed Nov. 14, 2006; which claims the benefit of U.S. Provisional Patent Application No. 60/736,923 filed on Nov. 14, 2005; each of which is hereby incorporated herein by reference in its entirety for all purposes.

STATEMENT OF GOVERNMENT INTERESTS

This invention was made with government support under National Institutes of Health grant number HG003170 and under U.S. Department of Energy grant number DE-FG02-02ER63445. The Government has certain rights in the invention.

FIELD

The present invention relates in general to novel methods of sequencing polynucleotides on a nanoarray.

BACKGROUND

Methods for generating spatially-clustered, support-attached nucleic acid amplicons include polony in situ PCR and emulsion PCR. In both cases, nucleic acid features as small as a micron can be produced, but both use limiting dilution to ensure clonal amplicons. This requirement limits the effective feature density per unit volume that can be achieved, as it is governed by Poisson statistics. Linear rolling circle amplification, multiple displacement amplification, and hyperbranched rolling circle amplification are all techniques which allow production of clonal amplicons without limiting dilution of template.

SUMMARY

The present invention is directed in part to a novel method for sequencing polynucleotides by generating and subsequently sequencing clonal, surface-bound nucleic acid amplicons which can be produced at much higher numbers per reaction volume than can be achieved using current methods known in the art.

In certain embodiments, methods for sequencing a polynucleotide immobilized on an array having a plurality of specific regions (e.g., a nanoarray) each having a defined diameter size including synthesizing a concatemer of a polynucleotide by rolling circle amplification, wherein the concatemer has a cross-sectional diameter greater than the diameter of a specific region, immobilizing the concatemer to the specific region to make an immobilized concatemer, and sequencing the immobilized concatemer, are provided. In certain aspects, the nucleic acid oligomer is DNA. In other aspects, optical magnification is used to determine the nucleic acid sequence of the clonally amplified concatemer.

In certain aspects, the concatemer has a cross-sectional diameter of at least 50 nanometers, at least 75 nanometers, at least 100 nanometers, at least 150 nanometers, at least 200 nanometers, at least 300 nanometers, at least 400 nanometers, at least 500 nanometers or greater.

In other aspects, one concatemer is immobilized at a specific region. In still other aspects, immobilization is performed by one or more of biotin-avidin capture, biotin-streptavidin capture, NHS-ester capture, thioether linkage, static charge interactions or van der Waals forces.

In certain aspects, the array has at least 100, 1,000, 10,000, 100,000, 1,000,000, 10,000,000, 100,000,000 or more specific regions. In still other aspects, at least 90, 900, 9,000, 90,000, 900,000, 9,000,000, 90,000,000, at least 95, 950, 9,500, 95,000, 950,000, 9,500,000, 95,000,000, at least 99, 990, 9,900, 99,000, 990,000, 9,900,000, 99,000,000 or more of the specific regions each contains one immobilized concatemer. In yet other aspects, one concatemer is immobilized at each of the specific regions.

In certain other embodiments, methods for sequencing a polynucleotide immobilized on an array (e.g., a nanoarray) having a plurality of specific regions each having a defined diameter size including synthesizing a concatemer of a polynucleotide by rolling circle amplification, wherein the concatemer has a cross-sectional diameter greater than the diameter of a specific region, immobilizing the concatemer to the specific region to make an immobilized concatemer, clonally amplifying the immobilized concatemer to make a clonally amplified concatemer, and sequencing the clonally amplified concatemer, are provided. In certain aspects, clonally amplifying is performed by a method selected from the group consisting of rolling circle amplification (e.g., hyperbranched rolling circle amplification, padlock probe rolling circle amplification and linear rolling circle amplification), multiple displacement amplification, thermophilic helicase-dependent amplification and bridge PCR.

In still other embodiments, methods for sequencing a polynucleotide immobilized on an array (e.g., a nanoarray) having a plurality of specific regions each having a defined diameter size of less than 300 nanometers including synthesizing a concatemer of a polynucleotide by rolling circle amplification, wherein the concatemer has a cross-sectional diameter of greater than 300 nanometers, immobilizing the concatemer to the specific region to make an immobilized concatemer, and sequencing the immobilized concatemer, are provided.

Further features and advantages of certain embodiments of the present invention will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION OF CERTAIN EMBODIMENTS

Figure 1:
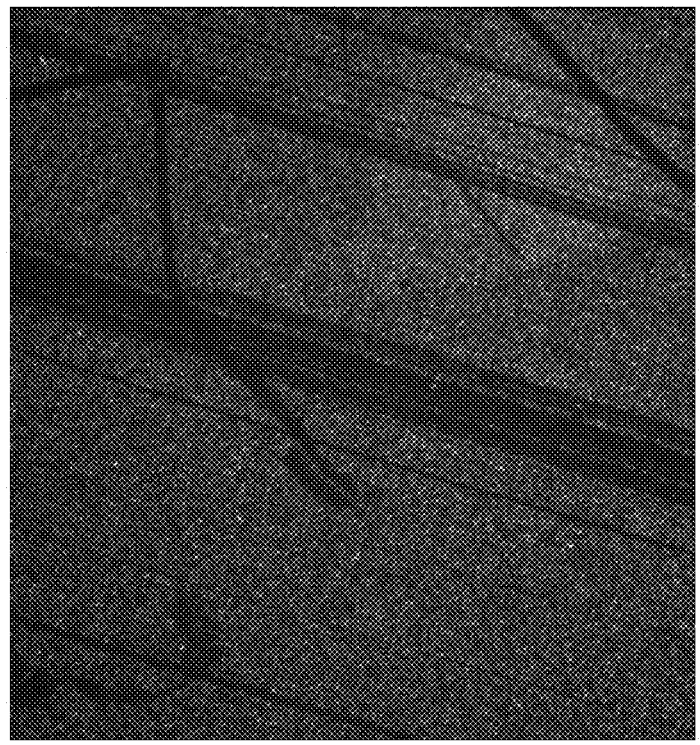
FIG. 1 depicts a false-color image of the clonal amplification of the concatemer-template. The slide was coated with the short primer, template concatemers (2 different species) were captured by hybridization, amplification by Strand Displacement Amplification (SDA) extension was performed, and clonality was assessed by single base extension (SBE). The image was acquired at 20× optical magnification (0.75 numerical aperture (NA)). The approximate size of one spot is 1 μm.
Figure 1:
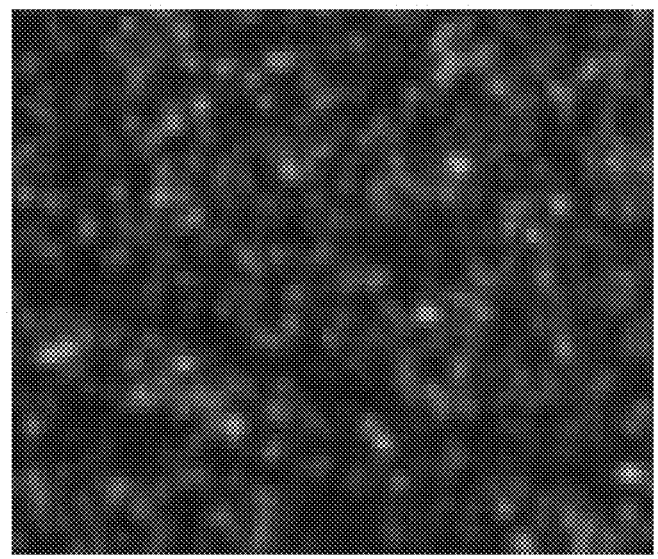
Figure 2:
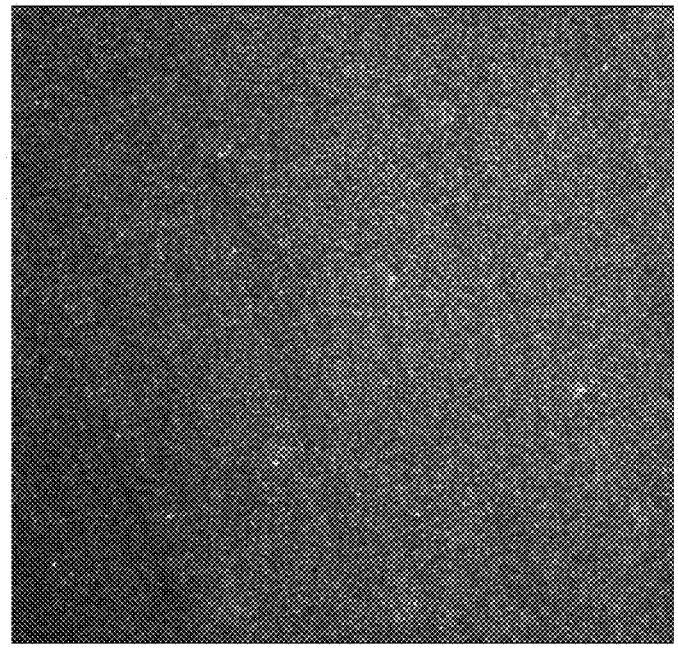
FIG. 2 depicts a false-color image of the clonal amplification of the concatemer-template. The slide was coated with the long primer, template concatemers (2 different species) were captured by hybridization, amplification by SDA extension was performed, and clonality was assessed by hybridization with three different fluorescently-labeled primers. Primers were a) a FITC-labeled sequence common to all amplicons, b) a Cy5-labeled sequence specific to amplicon species 1, and c) a Cy3-labeled sequenced specific for amplicon species 2. The FITC channel was used to align the three images. The image was acquired at 20× optical magnification (0.75 NA). The approximate size of one spot is 1 µm.
Figure 2:
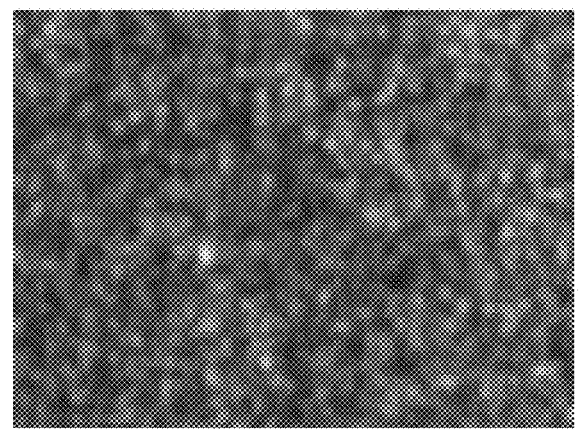
Figure 3:
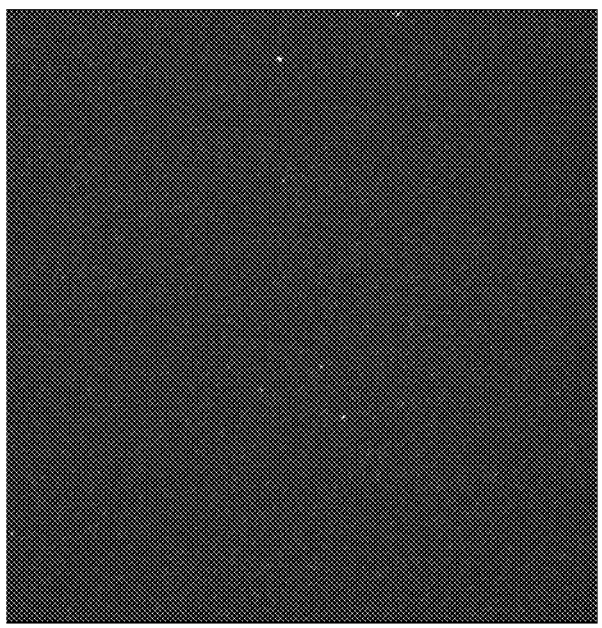
FIG. 3 depicts a Cy3 image of concatemer-template amplification. The large image on the top left is the amplification as performed in FIG. 2. The large image on the bottom right was taken after a second round of SDA. In brief, the primer extension was performed as above with the addition of 100 pmol of a reverse primer and reacted at 65° C. After the extension, the complementary strand was removed by denaturing it in 3 washes of boiling water. Detection was performed through hybridization. This experiment was also performed using thermophilic helicase-dependent amplification (tHDA) (Biohelix, using their protocol) and Vent Polymerase (cycling between 1 second at 94° C. and 5 minutes at 65° C.), with similar results. Image was acquired at 20× optical magnification (0.75 NA).
Figure 3:
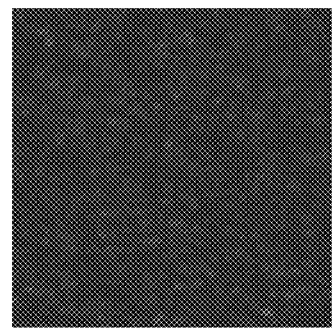
Figure 3:
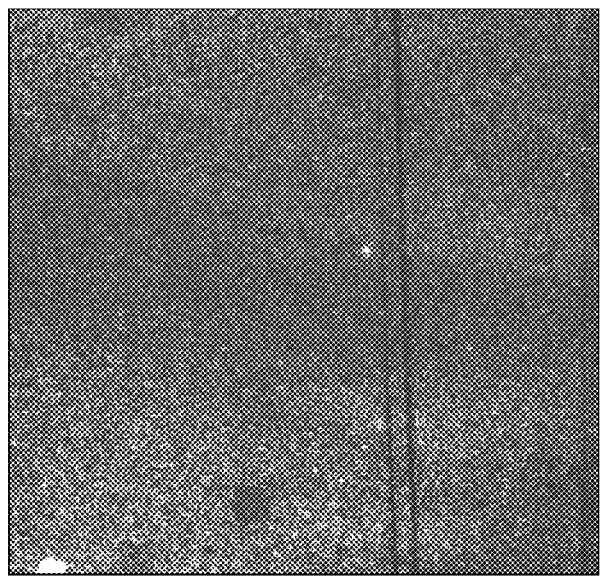
Figure 3:
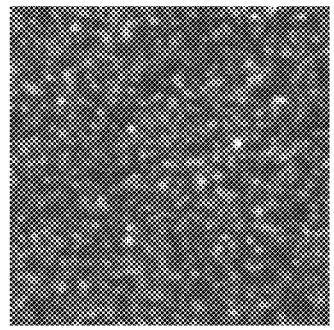
Figure 4:
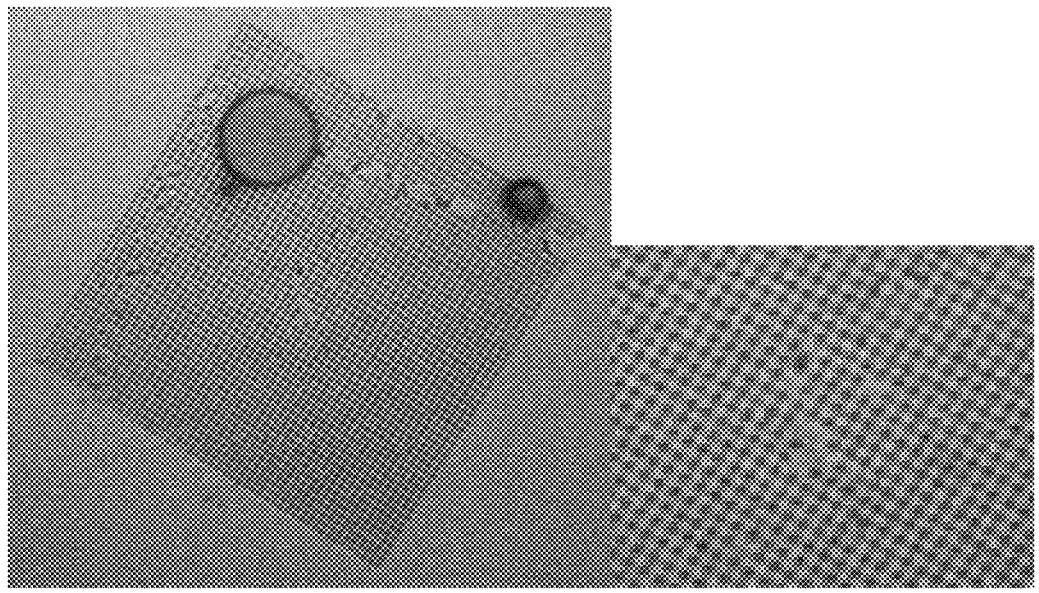
FIG. 4 depicts a brightfield micrograph of "nanogrid." The spots are 100×100 nm of NEB resist and the spacing is 1200 nm. The image was acquired at 20× optical magnification (0.75 NA).
Figure 5:
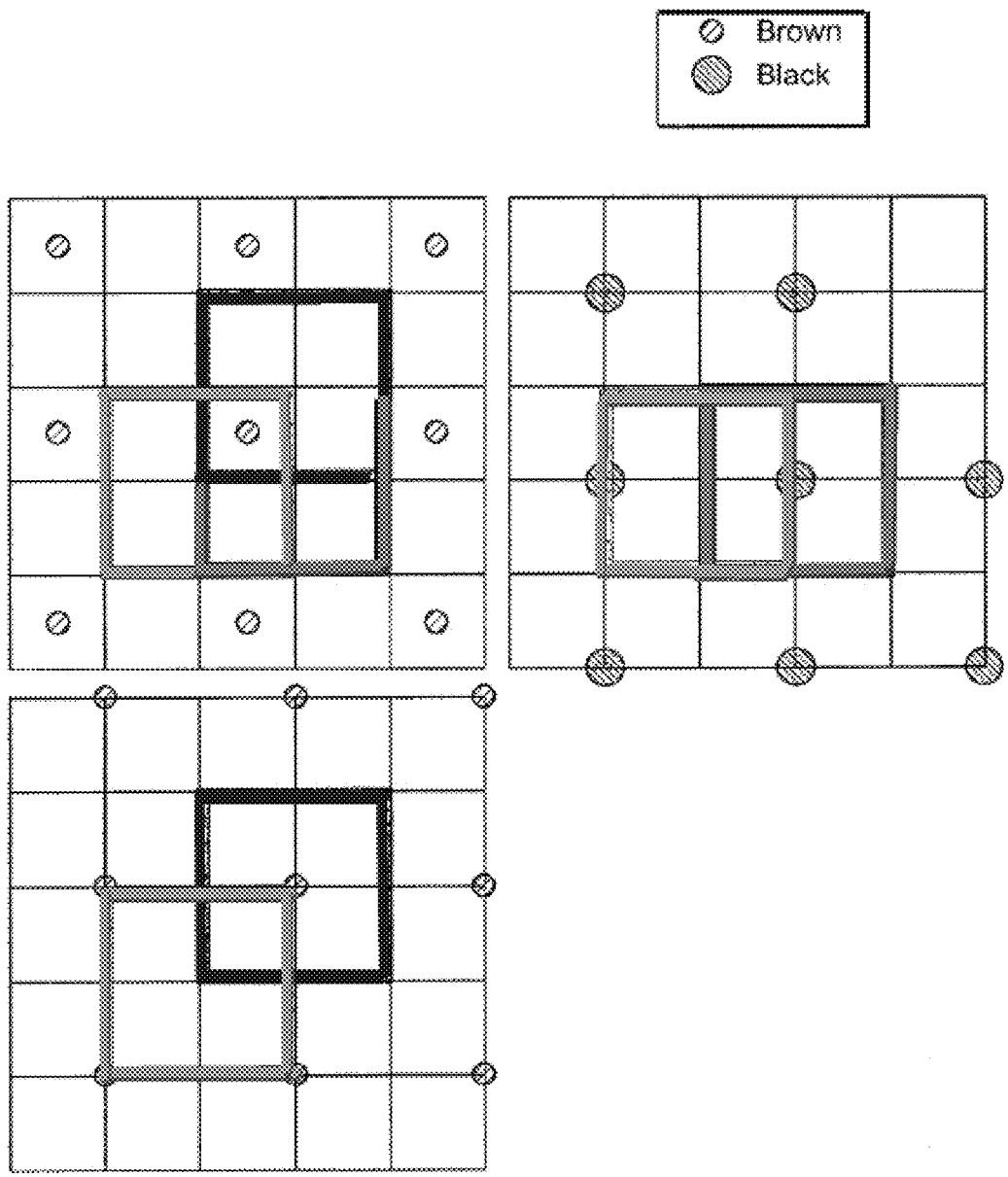
FIG. 5 depicts three offsets for the 4 pixels per polony strategy.
Figure 6:
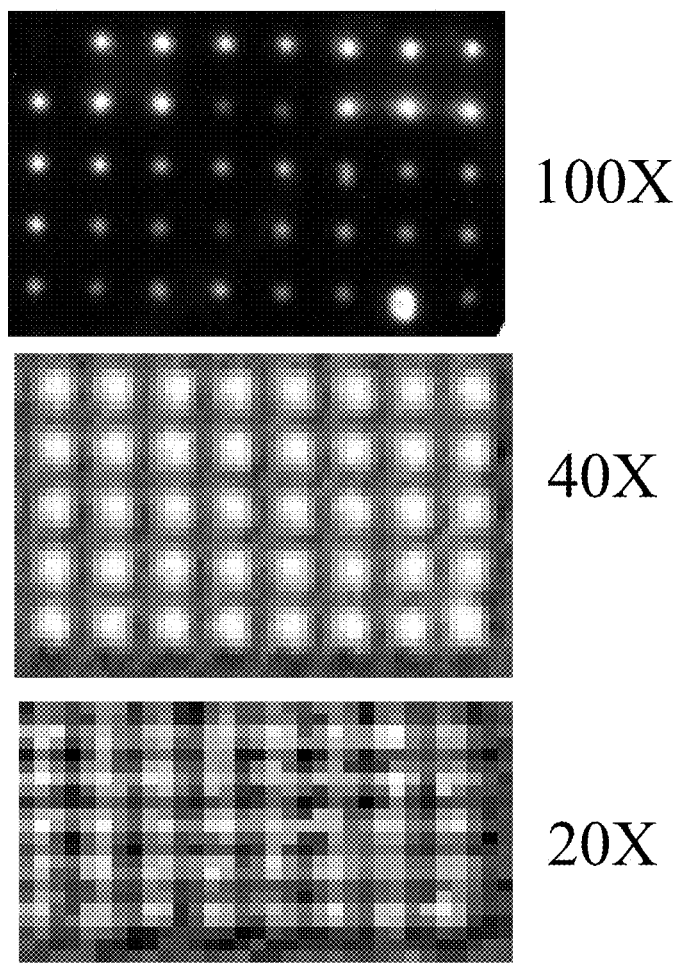
FIG. 6 depicts 100 nm spots at 1200 nm spacing. Fluorescent imaging resolution at various magnifications is indicated.
Figure 7:
FIG. 7 depicts two different species of concatemers generated by linear RCA to a slide that was covered with a field of primers.
Figure 7:
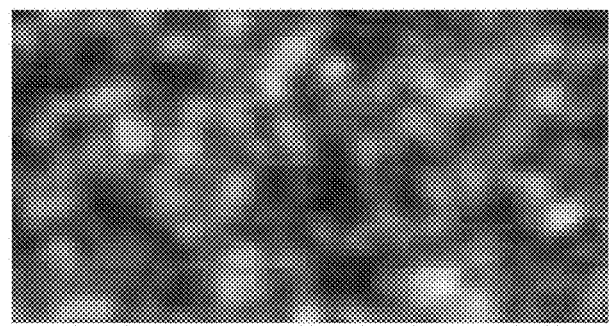

The present invention provides a novel nanotechnology useful for sequencing individual polynucleotides on a nanoarray.

Certain embodiments pertain to methods of performing rolling circle amplification (RCA) on polynucleotides to produce concatemers. Several suitable RCA methods are known in the art. For example, linear RCA amplifies circular DNA by polymerase extension of a complementary primer. This process generates concatemerized copies of the circular DNA template such that multiple copies of a DNA sequence arranged end to end in tandem are generated. Exponential RCA is similar to the linear process except that it uses a second primer of identical sequence to the DNA circle (Lizardi et al. (1998) *Nat. Genet.* 19:225). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (i.e., padlock RCA) (Nilsson et al. (1994) *Science* 265(5181): 2085). Hyperbranched RCA uses a second primer complementary to the rolling circle replication (RCR) product. This allows RCR products to be replicated by a strand-displacement mechanism, which can yield a billion-fold amplification in an isothermal reaction (Dahl et al. (2004) *Proc. Natl. Acad. Sci. U.S.A.* 101(13):4548).

In certain embodiments, methods of clonally amplifying concatemers, e.g., immobilized concatemers, are provided. Such methods include, but are not limited to, polymerase chain reaction (PCR), bridge PCR, thermophilic helicase-dependent amplification (tHDA), linear polymerase reactions, strand displacement amplification (e.g., multiple displacement amplification), RCA (e.g., hyperbranched RCA, padlock probe RCA, linear RCA and the like), nucleic acid sequence-based amplification (NASBA) and the like, which are disclosed in the following references: Nilsson et al. supra; Schweitzer et al. (2002) *Nat. Biotech.* 20:359; Demidov (2002) *Expert Rev. Mol. Diagn.* 2(6):89 (RCA); Mullis et al, U.S. Pat. Nos. 4,683,195; 4,965,188; 4,683,202; 4,800,159 (PCR); Gelfand et al., U.S. Pat. No. 5,210,015 (real-time PCR with "Taqman" probes); Wittwer et al., U.S. Pat. No. 6,174,670; Kacian et al., U.S. Pat. No. 5,399,491 (NASBA); Lizardi, U.S. Pat. No. 5,854,033; Aono et al., Japanese Patent Pub. JP 4-262799 (rolling circle amplification); Church, U.S. Pat. Nos. 6,432,360, 6,511,803 and U.S. Pat. No. 6,485,944 (replica amplification (e.g., "polony amplification"); and the like.

In certain embodiments, methods of determining the nucleic acid sequence of one or more clonally amplified concatemers are provided. Determination of the nucleic acid sequence of a clonally amplified concatemer can be performed using variety of sequencing methods known in the art including, but not limited to, sequencing by hybridization (SBH), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172)

Examples of detectable markers include various enzymes, prosthetic groups, fluorescent markers, luminescent markers, bioluminescent markers and the like. Examples of fluorescent proteins include, but are not limited to, yellow fluorescent protein (YFP), green fluorescence protein (GFP), cyan fluorescent protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like.

Certain embodiments are directed to synthesizing concatemers from polynucleotides. As used herein, the terms "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, 2,6-diaminopurine and the like. Nucleic acid molecules may also be modified at the base moiety, sugar moiety or phosphate backbone.

In certain embodiments methods of immobilizing one or more concatemers to an array are provided. "Nanoarray," "microarray" and "array" refer to a solid or semi-solid support having an array of spatially defined non-overlapping regions or sites that each contain an immobilized polynucleotide and/or a concatemer. Spatially defined sites may additionally be "addressable" in that its location and the identity of the immobilized polynucleotide and/or concatemer at that location is known or determinable. Typically, the polynucleotides and/or concatemers on microarrays are substantially or entirely single stranded and are covalently or noncovalently attached to the support, usually by a 5'-end or a 3'-end. In certain embodiments, the nucleic acid molecules are spaced at a distance from one another sufficient to permit the identification of discrete features of the array. Nucleic acids on the array may be non-overlapping or partially overlapping. Methods of transferring a nucleic acid pool to support media are described in U.S. Pat. No. 6,432,360.

"Support" can refer to a matrix upon which polynucleotides and/or concatemers of a nucleic acid array are placed. The support can be solid, semi-solid or a gel. As used herein, the term "solid substrate" includes, but is not limited to, materials such as glass silica, polymeric materials and the like. In certain embodiments, solid support materials include, but are not limited to, glass, polacryloylmorpholide, silica, controlled pore glass, polystyrene, polystyrene/latex, carboxyl modified Teflon, polymerized Langmuir Blodgett film, functionalized glass, Si, Ge, GaAs, GaP, $SiO_2$, $SiN_4$, modified silicon, or (poly)tetrafluoroethylene, (poly)vinylidendifluoride, polystyrene, polycarbonate, or combinations thereof.

Solid substrates include, but are not limited to, slides, plates, beads, particles, spheres, strands, sheets, tubing, containers (e.g., test tubes, microfuge tubes, bowls, trays and the like), capillaries, films, polymeric chips and the like. In some embodiments, at least one surface of the substrate is partially planar. In other embodiments it is desirable to physically separate regions of the substrate to delineate synthetic regions, for example with trenches, grooves, wells or the like.

As used herein, the term "semi-solid" includes, but is not limited to, a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

A support can include a variety of different binding moieties to permit the coupling of one or more polynucleotides and/or concatemers to the support. In certain aspects, a suitable binding moiety includes, but is not limited to, a capture moiety such as a hydrophobic compound, an oligonucleotide, an antibody or fragment of an antibody, a protein, a peptide, a chemical cross-linker, an intercalator and the like, or one or more elements of a capture pair, e.g., biotin-avidin, biotin-streptavidin, NHS-ester and the like, a thioether linkage, static charge interactions, van der Waals forces and the like. A support can be functionalized with any of a variety of functional groups known in the art. Commonly used chemical functional groups include, but are not limited to, carboxyl, amino, hydroxyl, hydrazide, amide, chloromethyl, epoxy, aldehyde and the like.

In certain embodiments, methods for arraying nucleic acid features and visualizing such arrays including, but not limited to, Picotiter arrays, polony sequencing arrays, and Quake arrays, are provided. The Picotiter imaging system uses a fiber optic array physically fused to the CCD detector, such that the feature density is limited by the detector pixel size, and the number of features is limited by the overall detector size. In practice, feature density is limited further because of bleed-through to adjacent array elements.

In the polony method, diffraction-limited optics lie between the array and the detector. Thus, the array can be as large as desired without requiring any increase in detector size. Feature size can be more easily matched to detector pixel size by adjusting optical magnification and numerical aperture (NA), but smaller features are desirable because they require less reagent use per feature (and this less cost per feature).

In the Quake array, features are diffraction-limited individual molecules, and so must be spaced by limiting dilution or some other physical means in order to be optically resolved. Thus, density is limited in theory by the resolution of the optics and pixel size relative to the optical magnification. In all cases, each useable feature requires tens to hundreds of pixels on the detector. A method to allow imaging of an ordered array of diffraction-limited amplicons is presented herein. The size of the amplicon and the spacing between amplicons can be easily controlled to match the optical resolution, magnification, and pixel size such that every pixel on the detector is occupied by a different nucleic acid feature.

To create a bead-free amplicon on a single-pixel array, a solid substrate to which the feature array can be anchored may be used. The surface of the substrate is functionalized in a pattern which will give rise to the ordered array. Methods of functionalization at the size scale described herein include, but are not limited to, electron-beam lithography and photolithography. For example, a grid of square patches, each 150 nm on edge, with a center-to-center spacing of 570 nm (optical resolution at 700 nm with NA=0.75 is 570 nm), will result in an array in which each diffraction-limited functionalized square corresponds to one pixel on the detector if the pixel size is 8 microns on edge and the optics have a NA of 0.75 and a magnification of 14 (20× objective and 0.7× relay). After suitable deconvolution to remove contributions from neighboring Airy patterns, the signal at each pixel on the detector will be a measurement of the signal at each functionalized square on the array.

Without intending to be bound by theory, the principle which guarantees clonality in this amplification method is "excluded volume." Each initial template molecule (monomeric) is first amplified by a strand-displacing polymerase to generate many copies that are covalently attached to each other. This 'concatemer' occupies a greater volume than the monomeric template, and this volume (or its cross-sectional area) is what defines the maximum size of each functionalized spot on the array. For example, without intending to be bound by theory, the product of a linear rolling circle amplification of a 135 base pair template molecule with Phi 29 polymerase is a single-stranded nucleic acid molecule of approximately 70,000 base pairs (Blanco et al (1989) *J. Biological Chemistry*) which would occupy a volume of having a cross-sectional diameter of approximately several hundred nanometers. If a surface of squares functionalized to bind the concatemers is saturated with concatemers, each square will bind exactly one molecule if its size is less than approximately several hundred nanometers on edge.

In typical diffraction-limited optical setups, with an NA in the range described above, this concatemer may not bear enough copies to be detected by, for example, fluorescence labeling of one site in the template in a short period of time. It is often necessary to perform a secondary amplification to provide enough clonal template molecules per functionalized spot for fast detection. One way to achieve this second amplification is by using functionalized spots which 'capture' the concatemer template molecules by hybridization (i.e., the surface is functionalized with oligonucleotides). In this example, the oligonucleotide attached to the substrate is complementary to sequence present in the concatemers. Once captured, a secondary exponential amplification is performed, e.g., using methods including, but not limited to, hyperbranched rolling circle amplification, multiple displacement amplification, bridge PCR and the like.

One possible limitation is that the amount of signal per pixel will be proportional to the size of the spot on the array (since the spots are below the diffraction limits of the optics) and any variation in size will result in signal variation. To alleviate this, each square can be replaced with a pair of concentric squares (or circles or any other shape) where the inner spot is functionalized with one group which serves to capture the concatemer template molecule, and the outer spot is functionalized with a second group which serves as an attachment point for the secondary amplification primer. The inner spot is of the size where clonality is maximal, i.e., smaller than the cross-sectional diameter of a concatemer, and the outer spot is of the size where signal is maximal, i.e., slightly smaller than the Airy disc of the objective lens used. Continuing the description above, the inner spot would be approximately 100 nm on edge, and the outer spot would be 550 nm on edge, with a center-to-center spacing of 570 nm. The same goal could be accomplished with a substrate coated uniformly with one functional type, i.e., an oligonucleotide that would allow for a secondary amplification, and had small spots of a second functional type that would serve as the point of initial attachment of the amplicon. In this case, one need only fabricate an array using one mask, which would define the small spots.

This invention is further illustrated by the following examples, which should not be construed as limiting. The contents of all references, patents and published patent applications cited throughout this application are hereby incorporated by reference in their entirety for all purposes.

EXAMPLE I

Template Preparation

Two 90 base pair oligomers (75 base pair like sequence, 15 base pair unique sequence) were ordered from IDT and are referred to as the templates. 10 pmol of the template was phosphorylated using 10 units of polynucleotide kinase (PNK) in 10 µl of T4 ligase buffer. The templates were then circularized using a 26 base pair guiding oligonucleotide and 5 units of AmpLigase in 50 µl of lX buffer cycling between 2 minutes at 94° C. and 10 minutes at 42° C. for 3 cycles. 1.5 µl of Exonuclease I (50 units) and 0.5 µl of Exonuclease III (50 units) were added to digest any remaining linear fragments. A rolling circle amplification (RCA) reaction was then performed in solution using 2 pmol of circular template, 2 pmol of primer, 25 nmol of dNTP and 20 units of Phi29 in 25 µl of 1× RepliPhi buffer. The reaction proceeded over the weekend (approximately 70 hours) at 30° C. One-third of the product was filtered through a Microcon YM-50 filter and then re-suspended in 200 µl of $dH_2O$. The product was quantified at 5 ng/µl using a Nanodrop spectrophotometer. Assuming 70,000 base pair molecules, a 220 pM solution was obtained.

EXAMPLE II

Slide Preparation

Slides were prepared using the protocol found at Example IX. Glass slides (Gold Seal) were cleaned for 0.5 to 2 hours in 2 N nitric acid. After rinsing in distilled water, the slides were soaked in distilled water for 5 to 15 minutes, and then washed once with acetone. The slides were silanized by immersing them for 15 minutes in a solution of 1% aminopropyl-methyl-diethoxysilane (Fluka) dissolved in 95% acetone. After washing the slides twice in acetone, the slides were baked for 30 minutes at 75° C. The surface of the slides was then activated by placing the slides in a solution of 0.5% 1,4-diphenylene-diisothiocyanate (PDC) (Fluka) dissolved in a solution consisting of 40 ml pyridine and 360 ml anhydrous N,N-dimethylformamide for 2 to 4 hours. The slides were then washed twice with methanol, twice with acetone, and stored in a dessicator until use. A custom-built arraying robot equipped with piezo-electric printheads was used to print the microarrays. After printing, the microarrays were incubated overnight at room temperature, then for 1 hour at 37° C. in a humidity chamber containing 300 mM $K_2HPO_4$, pH 9.0. The remainder of the PDC surface was inactivated by a 10 minute incubation in 1% ammonium hydroxide/0.1% SDS/200 mM NaCl. After washing in 4×SSC, the slides were neutralized in 6×SSPE/0.01% Triton X-100, washed twice in 4×SSC, then washed in 2×SSC and spun dry in a clinical centrifuge. Slides were stored in a closed box at room temperature until use.

EXAMPLE III

Coupling to the Slide

A 24 base pair oligomer with a 5' amino group and 6 carbon linker (short primer) and a 30 base pair oligomer with a 5' amino group and 12 carbon linker (long primer) were ordered from IDT and were re-suspended to a concentration of 100 µM in $dH_2O$. Either of the oligomers was coupled to the slide using a protocol based upon that found at Example IX. 5 µl of oligomer was added to 45 µl of 300 mM $K_2HPO_4$ and pipetted on to a coverslip, and the activated slide was placed on the coverslip and inverted. The slide was incubated at 25° C. for 5 minutes, 37° C. for 10 minutes, and the rest of the slide was then inactivated through placing it in blocking solution (1% $NH_4OH$, 0.1% SDS, 200 mM NaCl) for 10 minutes. The slides were then washed 4×SSC, 6×SSPE/0.01% Triton X-100, 4×SSC and 2×SSC. The slides were used immediately after the coupling.

EXAMPLE IV

DNA Hybridization

The hybridization of the concatemer template to the slide was adopted from the following protocol:
LRCA on Surface
 Objective: LRCA on surface with Bst DNA polymerase and Sequenase LRCA Reaction Conditions
 Sequenase version 2.0:
  40 mM TrisCl, pH 7.5
  23 mM $MgCl_2$
  25 mM NaCl
  10 mM DTT
  500 µM dNTPs
  0.02% Triton X-100
  100 µg/ml BSA
  4 µM SSB
  1 µM Sequenase version 2.0
  at 37° C. 15-30 minutes
 Bst DNA polymerase large fragment:
  20 mM TrisCl, pH 8.8 at 25° C.
  10 mM (NH4)2SO4
  4 mM MgSO4
  10 mM KCl
  500 µM dNTPs
  0.1% Triton X-100
  100 µg/ml BSA
  4 µM SSB (Optional)
  0.1 um Bst large fragment
  at 55° C. for 15-30 minutes
Reagents needed
Sequenase Version 2.0 reaction buffer:

| 1X | 5X |
|---|---|
| 40 mM TrisCl, pH 7.5 | 200 mM TrisCl, pH 7.5 |
| 2.5 mM $MgCl_2$ | 12.5 mM $MgCl_2$ |
| 25 mM NaCl | 125 mM NaCl |
| 10 mM1 DTT | 50 mM DTT |
| 0.02% Triton X-1120 | 0.1% Triton X-100 |

Bst Large Fragment reaction buffer:

| 1X | 5X |
|---|---|
| 20 mM TrisCl pH 8.8 | 100 mM TrisCl pH 8.8 |
| 10 mM $(NH_4)_2SO_4$ | 50 mM $(NH_4)_2SO_4$ |
| 4 mM MeSO_4 | 20 mM MgSO_4 |
| 10 mM KCl | 50 mM KCl |
| 0.1% Triton X-100 | 0.5% Triton X-100 |

Wash solutions
For Sequenase pre-reaction wash: to make 500 ml
 40 mM TrisCl, pH 7.5
 2.5 mM $MgCl_2$
 25 mM NaCl;
For Bst DNA Polymerase pre-reaction wash: to make 500 ml
 20 mM TrisCl, pH 8.8 at 25° C.
 10 mM $(NH_4)_2SO_4$
 4 mM $MgSO_4$
 10 mM KCl.
SSC-T: to make 1000 ml

2×SSC 0.05% Triton X-100

1 mg/ml degraded herring sperm DNA: to make 10 ml 10 mg degraded herring sperm DNA in 10 ml $H_2O$, boil to dissolve, centrifuge to remove any remaining solid residues.

Enzymes and accessory proteins:

Bst DNA polymerase (NEB, Vol. Act.: 8 U/µl

Sequenase Version 2.0 (Amersham, 13 U/µl)

SSB (Amersham, 2.2 µg/µl)

BSA (Roche, 20 mg/ml).

Hybridization of circles onto the primers immobilized an the glass surface.

1. 50 µl of 50 nM circle 2 was prepared in a hybridization solution 2.5 µl µM circle 2

10 µl 4×SSC or 6×SSPE+0.02% Triton X-100

37.5 µl $H_2O$ 2. 25 µl of the solution was pipetted onto a cover slip (2 cm×2 cm polypropylene or glass cover slip). The slide that had been coated with primers was brought down to the solution on the cover slip and inverted (with cover slip up).

3. The slide was incubated in a humidity chamber at 55° C. for 30-60 minutes.

4. The slide was washed briefly in LRCA wash solution (for Sequenase: 40 mM TrisCl, pH 7.5, 2.5 mM $MgCl_2$, and 25 mM NaCl; for Bst DNA Polymerase: 20 mM TrisCl, pH 8.8 at 25° C., 10 mM $(NH_4)_2SO_4$ 4 mM $MgSO_4$, 10 mM KCl). The solution was removed from the slide by a brief centrifugation.

LRCA reaction

5. Prepare 50 µl of LRCA reaction solution

For Sequenase reaction:

| | |
|---|---|
| 8 µl | 5X RCA reaction buffer |
| 2.5 µl | 10 mM dNTPs (Pharmacia, 10 mM in $H_2O$ pH 7.5) |
| 2.5 µl | 2 mg/ml BSA (diluted from 20 mg/ml BSA) |
| 1.7 µl | 116 µM SSB (Amersham Pharmacia Biorech 70032Z 2.2 µg/ml) |
| 5 µl | Sequenase (Amersham Pharmacia Biotech, 70032Z, 13 units/µl) |
| 30.3 µl | $H_2O$ |

For Bst DNA polymerase reaction

| | |
|---|---|
| 8 µl | 5X RCA reaction buffer |
| 2.5 µl | 10 mM dNTPs (Pharmacia, 10 mM in $H_2O$ pH 7.5) |
| 2.5 µl | 2 mg/ml BSA (diluted from 20 mg/ml BSA) |
| 1.7 µl | 116 µM SSB (Amersham Pharmacia Biorech, 70032Z, 2.2 µg/ml) |
| 5 µl | Bst DNA polymerase (NEB, 8 unit/µl) |
| 30.3 µl | $H_2O$ |

6. 25 µl of the solution was pipetted onto a cover slip (2 cm×2 cm polypropylene or glass cover slip). The slide that had been coated with primers was brought down to the solution on the cover slip and inverted (with cover slip up).

7. The slide was incubated in a humidity chamber at 37° C. for the Sequenase reaction and at 55° C. for the Bst reaction for 15-30 minutes.

8. The slide was rinsed in DI water to remove the cover slip. The slide was incubated in 2×SSC+0.1% SDS for 5 minutes, and washed 1× with SSC-T buffer for 5 minutes. Excess solution was removed from the slide by shaking or spinning. The slide was not allowed to dry out completely).

Detection of LRCA product by hybridization of fluorescently labeled oligo probes 9. 100 µl of probe hybridization solution was prepared (200 nM C2detley5 in SSC-T buffer+0.1 mg/ml degraded herring sperm DNA+0.1% BSA).

| | |
|---|---|
| 2 µl | 100 µM C2det1Cy5 |
| 10 µl | 1 mg/ml degraded herring sperm (Sigma) |
| 20 µl | 20X SSC |
| 5 µl | 2% BSA (i.e. 20 mg/ml BSA) |
| 5 µl | 1% Triton X-100 |
| 56 µl | $H_2O$ |

10. 40 µl of the solution was pipetted onto a cover slip (2 cm×2 cm polypropylene cover slip). The area of the slide that has been coated with primers was brought down to the solution on the cover slip and inverted (with cover slip up).

11. The slide was incubated in a humidity chamber at 500 for 30 minutes.

12. The cover slip was removed with a pair of forceps and washed in 2×SSC-T for 3 times on a shaker, 5 minutes for each wash. The slide was rinsed in 2×SSC, and blow dried with filtered compressed air or nitrogen. A drop of anti-fade solution was placed on the slide and it was covered with a cover slip.

13. The slide was scanned (Microarray Scanner) or imaged (microscope).

The following changes were made: 2.5 µl of each of the concatemer-templates were used in a volume of 50 µl, and were placed in a humidity chamber at 55° C. for 30 minutes.

EXAMPLE V

Extension

Strand displacement amplification (SDA) extension was performed using the above protocol for Bst Polymerase, with the change that SSB was not used and the reaction was run for 15 minutes.

EXAMPLE VI

Detection

Single Base Extension (SBE) to demonstrate clonality was performed according to the protocol found in Example XII. In brief, FISSEQ reverse primers were hybridized to the slide, and Klenow polymerase was used to extend one base with either Cy3 dATP or Cy5 dCTP.

Hybridization detection (to demonstrate clonality and single-strandedness of slide-bound amplicon) was performed by annealing a solution of three primers, an Oregon Green labeled primer that could hybridize to both templates, and a Cy3 and Cy5 labeled primer that could hybridize to only one type of primer. 75 pmoles of oligomer were used in 50 µl of 6×SSPE buffer and allowed to anneal at either 45° C. or 55° C. (depending upon the primer set) for 5 minutes, and washed 2× in Wash 1E (100 mM Tris pH 7.5, 20 mM EDTA, 500 mM KCl).

Slides were imaged using an epifluorescence microscope with an Orca II-ER CCD camera and Plan Apo 20×NA 0.75 objective.

EXAMPLE VII

Rolony-Sequencing

Rolling circle amplification (RCA) can be used to create a dense structure with maximal fluorescence, as well as a suitable structure for "excluded volume cloning."

Rolling-circle-colony, i.e., rolony plus nanogrids, can achieve a 70 to 700-fold scale-up. 1 Mbp per cycle has been obtained from 750 M pixels. The inefficiency of bead-emulsion amplification makes its cost impact significant. More importantly, the beads used in bead-emulsion amplification may be less fluorescent and do not provide the best way to interface with nanogrids. That is, a spherical bead has a tiny point of contact and a tendency to roll, while each RCA blob should adhere to one entire 70 nm nano-grid-patch. As a dilute wave of RCAs hits the first row of nanopatches, each RCA will completely cover one patch, and, accordingly, be clonal.

The current beads have r=500 nm; a ds-150 bp amplicon molecule=2×2×50 nm. Without intending to be bound by theory, the maximum number of amplicon molecules in the hemispherical annulus facing the camera would be 433K (actually less than 40K since the PCR intensity is 10-fold lower than oligo-loaded beads), while a r=400 nm tight RCA sphere could have 1.3M amplicons. Without intending to be bound by theory, assuming that the monomer-circle to single-stranded, linear-RCA phase yields 1000 tandem amplicons, then another 1000-fold in the single-strand to second-strand (hyperbranch) phase (on or off the slide) could be achieved. A 70 nm square on the slide surface could consist of 100 to 1000 primers (An et al. (2005) *J. Biol. Chem.* 280(32):28952).

Polycations (Mg++ and/or polyamines) can be used to contract the RCA-sphere during imaging. Low-salt will expand it to allow oligo replacement & ligation reactions.

Nano-imprinting (See, e.g., Jung et al. (2005) *Langmuir* 21(14):6127; Yan et al. (2005) *Nano. Lett.* 5(4):745); Evelyn et al. (2005) *Biomaterials* 26(26):5405; Luesebrink et al. (2005) *J. Nanosci. Nanotechnol.* 5(6):864; Ge et al. (2005) *Nano. Lett.* 5(1):179; Liang et al. (2005) *Nano Lett.* 5(3):527; Jung et al. (2005) *Langmuir* 21(4):1158; Lenhert et al. (2005) *Biomaterials* 26(5):563) can be used to make a prototype simply by delivering oligo-attachment chemicals to the glass surface with a fine needle on a mm grid and then just measuring the patch sizes under the microscope. Then the ability to clonally mask the nanopatches could be quickly addressed by using a mixture of two colored RCAs. A third color could be used for small oligos which could show the size of each nanopatch. Improved pattern transfer in nanoimprint lithography at 30 nm half-pitch by substrate-surface functionalization. Using 4 or 9 pixels-per-rolony can yield a 100-fold cost improvement (over 750 pixels per polony).

Given that 100-200 nm nanospots can be fabricated on an 800 nm grid (center-to-center with approximately 20 nm precision) and that a 8000 nm CCD pixel corresponds to 400 nm (at 20×) on the gridded-slide, the X and Y axis positioning has a precision of 1 micron (3 pixels). To orient oneself in the 2 billion nanospots in a 60×24 mm coverslip (250,000 spots per CCD frame), are fiducial alignment features will be designed into the grid. Imaging software will use these to achieve within one pixel precision. Then 4 adjacent pixels will be summed with 3 offsets (red, green, blue below) to determine which one works the best for a given frame. Test images may be made from scratch or from previous bead-polony sequencing. Spot-spacing, optics, and CCD pixel spacing can be coordinated precisely to optimize data collection efficiency, minimizing photons spilling over from adjacent rolonies and minimizing the number of pixels without any data.

1) Patterning—100 nm feature sizes can be generated on a 1.2 um or 2.4 um pitch. Arrays are currently 25×25 on silicon. Spots aren't perfectly square. There are big spots in the middle of some arrays that to blank the beam in the middle of patterning. In certain embodiments, these will not be in the arrays.

2) Chemistry—The surface is fluorinated (C8H4F13) in the negative patterns. Spots are functionalized with propylamine. Isothiocyanate coupling verified by RITC binding. All surfaces are one monolayer, measured by ellipsometry and AFM.

3) Assuming there is a fluor every 10 nm (which is a reasonable assumption based on the size of rhodamine compared to a phosphoramidite), there are only 100 fluors per spot. Polony amplification can increase this, for two reasons. First, more fluors will be present. Second, many fluors will be farther away from the surface, thereby limiting quenching.

NEB resist may be used on glass to eliminate quenching. Without intending to be bound by theory, NHS-NHS coupling may be more bio-stable than thiourea.

Millions of spots per chip may be obtained, costing about $1M. Once the volume is high nanoimprint may be used (cost ~$2M). Without intending to be bound by theory, one could make 1 per minute. Optical or x-ray lithography systems are about $80M to reach 100 nm. Another alternative is nanosphere lithography (NSL) using evaporated metal as the resist. A metal evaporator would cost about $100K.

In one embodiment, the CCD grid is 8 microns center-to-center. Using a 20× objective that would mean 400 nm center to center on the slide. A 10× objective which would be 800 nm. A 1200 nm (an integral multiple of 400) can also be used.

For the spot shape, a circle or a square may be used. For spot size, 50 nm, 75 nm, 100 nm and the like (full width) may be used. In certain embodiments, "isolated" spots will be used to check cross-talk (e.g. a 4800 nm grid). In certain embodiments, three separate glass or quartz slides (or the Si wafer equivalent) will be used on each run, enabling one to achieve a bright image, another for a more typical DNA polony image, plus one in case either of those two fails.

In certain embodiments, a set would be 3 slides each with 3 spot sizes (50, 75, 100) at 6 spacings (399.6, 400, 400.4, 800, 1200, 4800). In other embodiments other arrangements, e.g. one slide with two spot sizes (50,100) at 2 spacings (400, 800), will be used.

Two different species of concatemers generated by linear RCA were hybridized to a slide that was covered with a field of primers, and ran a reaction with Bst polymerase for 30 minutes. The result (when assayed with SBE using Cy3 and Cy5 dNTPs with a FITC primer) was a dense field of ~1 micron spots covering the entire slide. Almost every spot on the slide was either Cy3 or Cy5 without any overlapping signal.

34 base reads, 1200 nm center-to-center, 6e10 bases (10× diploid human genome) would mean $35. The main cost issue being addressed was the need for something other than e-beam once billions of spots are achieved, since e-beam might take a few days at $4000 per day. A nanoimprinting machine developed by Eric Wilhelm is also capable of microcontact printing. Commercial single layer photolith at 65 nm is approximately $0.5 per cm² per layer. E-beam can be used to make a Photomask, an Imprint or a micro-contact master for mass production.

EXAMPLE VIII

Synthesis of the DNA for the Rpn4 PBM Proof-of-Principle Microarrays

The following Cy3-labeled oligonucleotide (Operon) was spotted at 10 µM in 150 mM $K_2HPO_4$, pH 9.0 for alignment purposes: 5' TCAGAACTCACCTGTTAGAC 3' (SEQ ID NO:1). This oligo was spotted to create a series of alignment spots, essentially as described previously (Bulyk et al. (2001) *Proc. Natl. Acad. Sci. U.S.A.* 98(13):7158). The following set of oligonucleotides was synthesized (Operon) to represent various positive and negative control spots for binding by the yeast transcription factor Rpn4. The following sequences are listed 5' to 3':

```
                                              (SEQ ID NO: 2)
NNNNNNNNNNNTTCTTCTTCTTCNNNNNNNNNNNTCAAGTCAATCGGTCC;

(SEQ ID NO: 3)
NNNNNNNNNNNTCNTCNTCNTCNNNNNNNNNNNTCAAGTCAATCGGTCC;

(SEQ ID NO: 4)
NNNNNNNNNNNTTCTTCTTCNNNNNNNNNNNTCAAGTCAATCGGTCC;

(SEQ ID NO: 5)
NNNNNNNNNNNTCNTCNTCNNNNNNNNNNNTCAAGTCAATCGGTCC;

(SEQ ID NO: 6)
NNNNNNNNNNNTTCTTCNNNNNNNNNNNTCAAGTCAATCGGTCC;

(SEQ ID NO: 7)
NNNNNNNNNNNTCNTCNNNNNNNNNNNTCAAGTCAATCGGTCC;

(SEQ ID NO: 8)
NNNNNNNNNNNCTCATCNNNNNNNNNNNTCAAGTCAATCGGTCC;

(SEQ ID NO: 9)
NNNNNNNNNNNCTCATCCTCATCNNNNNNNNNNNTCAAGTCAATCGGTCC;

(SEQ ID NO: 10)
NNNNNNNNNNNWTTTGCCACCNNNNNNNNNNNTCAAGTCAATCGGTCC;

(SEQ ID NO: 11)
NNNNNNNNNNNNNYRCCRCYRNNNNNNNNNNNTCAAGTCAATCGGTCC;

(SEQ ID NO: 12)
NNNNNNNNNNNNNCGCCACCNNNNNNNNNNNTCAAGTCAATCGGTCC;

(SEQ ID NO: 13)
NNNNNNNNNNNNNNNNNNNNNNNNNNNNNNNTCAAGTCAATCGGTCC;

(SEQ ID NO: 14)
NNNNNNNNNNNTGTCCTACTGCTNNNNNNNNNNNTCAAGTCAATCGGTCC;

(SEQ ID NO: 15)
NNNNNNNNNNNYYYYYYYYYYYYNNNNNNNNNNNTCAAGTCAATCGGTCC;

(SEQ ID NO: 16)
NNNNNNNNNNNYYYYYYYYYNNNNNNNNNNNTCAAGTCAATCGGTCC;
and
                                              (SEQ ID NO: 17)
NNNNNNNNNNNYYYYYNNNNNNNNNNNTCAAGTCAATCGGTCC.
```

The following 16-mer was synthesized with a 5' amino linker and HPLC-purified (Operon) and used as a universal primer: 5' GGACCGATTGACTTGA 3' (SEQ ID NO:18). Each of the 12 unmodified full-length oligonucleotides listed above was combined with the amino-tagged 16-mer in a 2:1 molar ratio in a Sequenase reaction using 20 µM 16-mer. The completed extension reactions were exchanged into 150 mM $K_2HPO_4$, pH 9.0 using CentriSpin-10 spin columns (Princeton Separations, Inc.). The resulting samples were transferred to a 384-well plate for arraying.

EXAMPLE IX

Microarray Preparation for the Rpn4 PBM Proof-of-Principle Microarrays

Glass slides (Gold Seal) were cleaned for 0.5 to 2 hrs in 2 N nitric acid. After rinsing in distilled water, the slides were soaked in distilled water for 5 to 15 minutes, and then washed once with acetone. The slides were silanized by immersing them for 15 minutes in a solution of 1% aminopropyl-methyl-diethoxysilane (Fluka) dissolved in 95% acetone. After washing the slides twice in acetone, the slides were baked for 30 minutes at 75° C. The surface of the slides was then activated by placing the slides in a solution of 0.5% 1,4-diphenylene-diisothiocyanate (PDC) (Fluka) dissolved in a solution consisting of 40 ml pyridine and 360 ml anhydrous N,N-dimethylformamide for 2 to 4 hours. The slides were then washed twice with methanol, twice with acetone, and stored in a dessicator until use. A custom-built arraying robot equipped with piezo-electric printheads was used to print the microarrays. After printing, the microarrays were incubated overnight at room temperature, then for 1 hour at 37° C. in a humidity chamber containing 300 mM $K_2HPO_4$, pH 9.0. The remainder of the PDC surface was inactivated by a 10 minute incubation in 1% ammonium hydroxide/0.1% SDS/200 mM NaCl. After washing in 4×SSC, the slides were neutralized in 6×SSPE/0.01% Triton X-100, washed twice in 4×SSC, then washed in 2×SSC and spun dry in a clinical centrifuge. Slides were stored in a closed box at room temperature until use.

EXAMPLE X

PBM Data Quality Control Filters

Total # of spots on microarrays=8192

(1) Only those spots with known sequence were considered. Empty, blank and control spots, and also spots for which the Research Genetics primers did not map well to the claimed intergenic region, thus possibly leading to poor PCR quality, were removed.

Total # of possible spots considered=6814

(2) A number of spot filters were employed based on the SybrGreen I data. The following numbers of spots passed each of the following filters, applied in the following order:

1. Raw data spot quality (flags; intraspot SD/mean; 50% pixels>B+2SD): 6683

2. Variability (inter-array SD/mean<=1): 6683

3. Length<1500: 6654

4. Intensity (SybrGreenI intensity>=10000): 6625

5. Density (SybrGreenI/length>=61; this is 10% of the array average): 6494

Thus, the total number of spots with acceptable SybrGreen I data was 6494.

(3) A number of spot filters were employed based on the PBM data.

1. Raw data spot quality (flags; intra-spot SD/median greater than 2)

2. Variability (inter-array SD/mean greater than 1)

3. Must have SybrGreen data in order to calculate log ratio

TABLE 1

| dataset | array 1 (number of spots filtered out due to reason 1 above) | array 2 (number of spots filtered out due to reason 1 above) | array 3 (number of spots filtered out due to reason 1 above) | total number of spots removed (required data in greater than or equal to 2 out of 3 arrays) | additional number of spots removed due to reason 2 above (i.e., due to variability) | additional number of spots filtered out due to SybrGreen I filters (reasons 3-5 above) |
|---|---|---|---|---|---|---|
| SybrGreen I | 150 | 244 | 132 | 131 | 0 | 189 |
| Rap1 | 40 | 94 | 511 | 23 | 21 | — |
| Abf1 | 1107 | 320 | 439 | 280 | 100 | — |
| Mig1 | 126 | 95 | 92 | 65 | 9 | — |

(4) Duplicate spots were removed. In cases where there were identical spots, the one with PBM data and higher absolute SybrGreen I signal intensity was kept. The total number of possible non-duplicate spots was 6723.

TABLE 2

| Dataset | non-duplicate spots with SybrGreen I (and PBM) data | Average SD/mean |
|---|---|---|
| SybrGreen I | 6449 (95.9%) | 0.130 |
| Rap1 | 6431 (95.7%) | 0.323 |
| Abf1 | 6142 (91.4%) | 0.282 |
| Mig1 | 6442 (95.8%) | 0.202 |

EXAMPLE XI

Electrophoretic Mobility Shift Assays

Complementary biotinylated DNA oligonucleotides, each 45 base pairs in length, were synthesized such that they contained the predicted Rap1 binding site, flanked by its native flanking sequence from the given intergenic region. A positive control probe containing a known Rap1 binding site and a negative control probe lacking a Rap1 binding site were also synthesized and used in EMSAs.

The oligonucleotides were diluted in TE, pH 8.0 to a working stock of 10 µM. The working stocks for each of the two complementary oligonucleotides (designated "-U" for biotinylated "upper", and "-L", for "lower") were combined in the following ratios, respectively: 1:2 for both control probes and iYPL221W, and 1:5 for the probe iYLL051C. The solutions were then brought to a final volume of 20 µl with TE, pH 8.0. Each such pair of single-stranded complementary oligonucleotides were annealed in a thermocycler according to the following thermocycling protocol, resulting in approximately 1 µM final concentration of each biotinylated, double-stranded oligonucleotide:
(1) 94° C. for 3 minutes
(2) Ramp down 1° C. in 10 seconds (0.1° C. per second)
(3) Hold at current temperature for 1 minute
(4) Repeat Steps 2 and 3 to 37° C.
(5) 3° C. Hold The annealed oligonucleotide probes were filtered using Millipore's Microcon YM-100 (100,000 molecular weight cutoff) before use in EMSAs.

The sequences of the oligonucleotides that we used for the Rap1 EMSA probes were as follows:
Positive Control Rap1 Binding Site:

Rap1-iYHL038C-U:
(SEQ ID NO: 19)
ACTTTCACTAAATACACCCATACACACCAATCTTGGATTCTACTC

Rap1-iYHL038C-L
(SEQ ID NO: 20)
GAGTAGAATCCAAGATTGGTGTGTATGGGTGTATTTAGTGAAAGT

Negative Control Rap1 Binding Site:

Rap1-iYLR288C-U
(SEQ ID NO: 21)
TCCGTATGTTTATGTTGCTATTTTGATGTAAATAAAAAAGTTGAA

Rap1-iYLR288C-L
(SEQ ID NO: 22)
TTCAACTTTTTTATTTACATCAAAATAGCAACATAAACATACGGA

Interesting Probes:
Significant PBM p-value with poor match to PBM derived Rap1 binding site:

Rap1-iYLL051C-U
(SEQ ID NO: 23)
AAACAATGCCCACTAGCCGGGGTGTACGGGACCTTAAATCTAAGT

Rap1-iYLL051C-L
(SEQ ID NO: 24)
ACTTAGATTTAAGGTCCCGTACACCCCGGCTAGTGGGCATTGTTT

Significant PBM p-value with poor match to TRANSFAC derived Rap1 binding site:
Rap1-iYPL221W-U
(SEQ ID NO: 25)
GGGCATACTTTACGGGGTGCACGGATTTTAGCAGTCTTTTTCTTT Rap1-iYPL221W-L
(SEQ ID NO: 26)
AAAGAAAAAGACTGCTAAAATCCGTGCACCCCGTAAAGTATGCCC Electrophoretic mobility shift assays (EMSAs) were performed according to manufacturer's protocols for the LightShift Chemiluminescent EMSA Kit (Pierce, Rockford, Ill.). The "+" lanes correspond to EMSA reactions that contained approximately 350 nM DNA probe and approximately 29 nM GST-His6-Rap1. The 'no protein' EMSA reactions ("−" lanes) contained approximately 350 nM DNA probe and no Rap1 protein. All EMSA binding reactions contained 1× LightShift Binding Buffer, 0.05 µg/µl poly(dI-dC) nonspecific DNA competitor, 2.5% glycerol, 50 mM KCl, 0.2 µg/µl BSA, 0.05% NP-40, and 0.5 mM zinc acetate. The 20 µl binding reactions were allowed to sit at room temperature for 1 hour. Subsequently, 2.2 µl of NOVEX® 5× Hi-Density TBE Sample Buffer (Invitrogen, Carlsbad, Calif.) was added to the reactions, and 12.5 µl of the reaction was run on a 6% polyacrylamide DNA retardation gel (Invitrogen, Carlsbad, Calif.) in 0.5×TBE at 100 V for 50 minutes. The contents of the gel were transferred to a BIODYNE® B Pre-cut Modified Nylon Membrane, 0.45 µM (Pierce, Rockford, Ill.), and UV-crosslinked to the membrane at 120 µJ/cm². The membrane was then treated with developing buffers (LightShift Blocking Buffer with stabilized Streptavidin-Horse Radish Peroxidase conjugate, Wash Buffer, Substrate Equilibration Buffer, Luminol/Enhancer Solution and Peroxide Solution) according to manufacturer's protocols. The blot was promptly exposed to Kodak film for ½ second, which was then developed.

EXAMPLE XII

Hybridization/Single Base Extension

Denaturation

At the conclusion of the PCR reaction, amplicons were present in double-stranded form, with one strand anchored to the gel via the acrydite modification. Denaturation enabled removal of the unanchored strand, such that the remaining strand could be free to serve as a template for hybridization and sequencing reactions.

1. The following 70% formamide denaturation solution was prepared directly in a plastic Coplin jar (a dedicated Coplin jar was generally kept for use with formamide only): 2 mL 20×SSC, 28 mL Formamide, and 10 mL dH₂O. The solution was mixed by stirring with one of the pipettes.
2. The solution was heated (without a lid) to 70° C. in a microwave (using a thermometer to check). Typically only 30 seconds or so was required to heat formamide to this temperature. Care was taken not to boil the formamide over.
3. The slides were deposited into the heated formamide solution, and incubated in the Coplin jar for 15 minutes with shaking in a 70° C. incubator.
4. The jar was removed from the incubator and the slides were transferred to a separate plastic Coplin jar.
5. The slides were washed one time for 3 minutes in dH₂O on a shaker.
6. The slides were washed two times for four minutes each time in Wash 1E on a shaker.

Annealing

In this step, a sequencing primer (or labeled probe) was annealed to a specific location within the now-single-stranded PCR. Although it was possible to use the unmodified amplification primer itself as the sequencing primer, it was generally determined to be advisable to use a sequencing primer that was internal to the PCR product (largely to avoid incidental sequencing of spurious PCR products, primer-dimer formation, and the like).

1. The following annealing mix was prepared: 1194 µL 6×SSPE with Triton X-100; and 6 µL sequencing primer (100 µM). The annealing mix was usually prepared fresh, but it was determined that it could be stored at room temperature. Storing at −20° C. was possible, but that could result in precipitation of salts out of solution.
2. The slides were removed from the wash 1E-filled Coplin jar and the edges were dried with a Kim Wipe, taking care not to touch the gel.
3. Blue FrameSeal chamber base was applied to the slides.
4. The blunt end of a pair of tweezers was used to seal the chamber and remove the plastic surface covering sticky area.
5. 125 µL of annealing mix was applied to the center of each gel.
6. The chamber with covered with a plastic seal. The liquid was spread evenly over the surface of the gel.
7. The blunt end of a pair of tweezers was used to seal the chamber and cover.
8. The slides were placed in a thermal cycler with labels facing out.
9. The following annealing program was run: 94° C. for 6 minutes, 56° C. forever.
10. After the 56° C. step had run for 15 to 20 minutes, the slides were individually removed from the slide-block, the FrameSeal chambers were QUICKLY pulled off, and the slides were immediately dunked into a Coplin jar filled with Wash 1E. This diluted away excess sequencing primer before the temperature could drop in order to limit the amount of non-specific binding.
11. The slides were washed two times for four minutes each time with shaking in Wash 1E.
12. For labeled hybridization probes, scanning was then performed. For other applications, single base extension was performed.

Extension

The selection of a specific Cy-label and dNTP combinations was dependent upon exactly what was being sequenced in a specific experiment. Cy-labeled dNTPs are NOT terminators, and experiments were designed accordingly. More than one labeled or unlabeled base could be included in an extension reaction. A typical genotyping experiment, for example, could include 2 dNTPs (one Cy3 labeled and one Cy5 labeled). The signal-to-noise ratios obtained using Cy5-labeled bases was considerably better than using Cy3. Another option was to extend with a single Cy5-labeled base, scan the gel, and then perform a second extension reaction with the other base. The genotypes could be determined by image processing after the fact. Even when attempting to probe, rather than sequence over a SNP, Cy-labeled hybridization probes were generally avoided because labeled primers are expensive. Instead, an SBE was performed over a known base.

1. The following extension mix was prepared at room temperature (approximately 45 µL of extension mix was needed per slide). The formula for 100 µL of extension mix is as follows: 1 µL Klenow (50 U/µL); 1 µL SSB; 0.5 µL Cy5-dNTP or Cy3-dNTP (100 µM) (this is more than enough base; lower concentrations can even give better signal-to-noise); and 98.5 µL 1× Klenow Buffer.
2. Slides were equilibrated by replacing the buffer in the Coplin jar with 1× Klenow Buffer for 2 to 3 minutes.
3. Slides were removed and the edges were dried with a Kim Wipe, taking care not to touch the gel. This kept the mix from being diluted or running off the gel.
4. 45 µL of extension mix was added to each slide.
5. Each reaction was allowed to proceed for 2 minutes. The slides were tilted around a bit such that the extension mix covered the surface of the gel.
6. The slides were washed slides two times for four minutes each time with shaking in Wash 1E.

7. The slides were then ready for scanning.

Scanning

The following protocol was typically performed with Perkin-Elmer and Axon instruments, but is suitable for use with a variety of scanning equipment.

Gels could be scanned dry or wet (the latter under a cover-slip). When it was planned to reuse amplified gels (e.g., to denature and re-anneal for a second round of sequencing, for example), the slides were usually scanned wet so that they did not dry out. One important aspect for keeping the gels stable over repeated use was to always dip the slides in liquid (e.g., Wash 1E) immediately before removing the coverslip. It was determined that gel damage over repeated uses of a given slide was primarily a consequence of removing the coverslip from a dry-gel after scanning.

Generally, a good signal-to-noise ratio was obtained using modest power and PMT settings (e.g., 50:1 signal-to-noise with Cy5 dye SBE scanned at 80/80). The focus could often differ from that which was required for scanning microarrays, so this was an important parameter to adjust.

EXAMPLE XIII

Sequencing by Ligation on Linear RCA Amplicons

Figure 8:
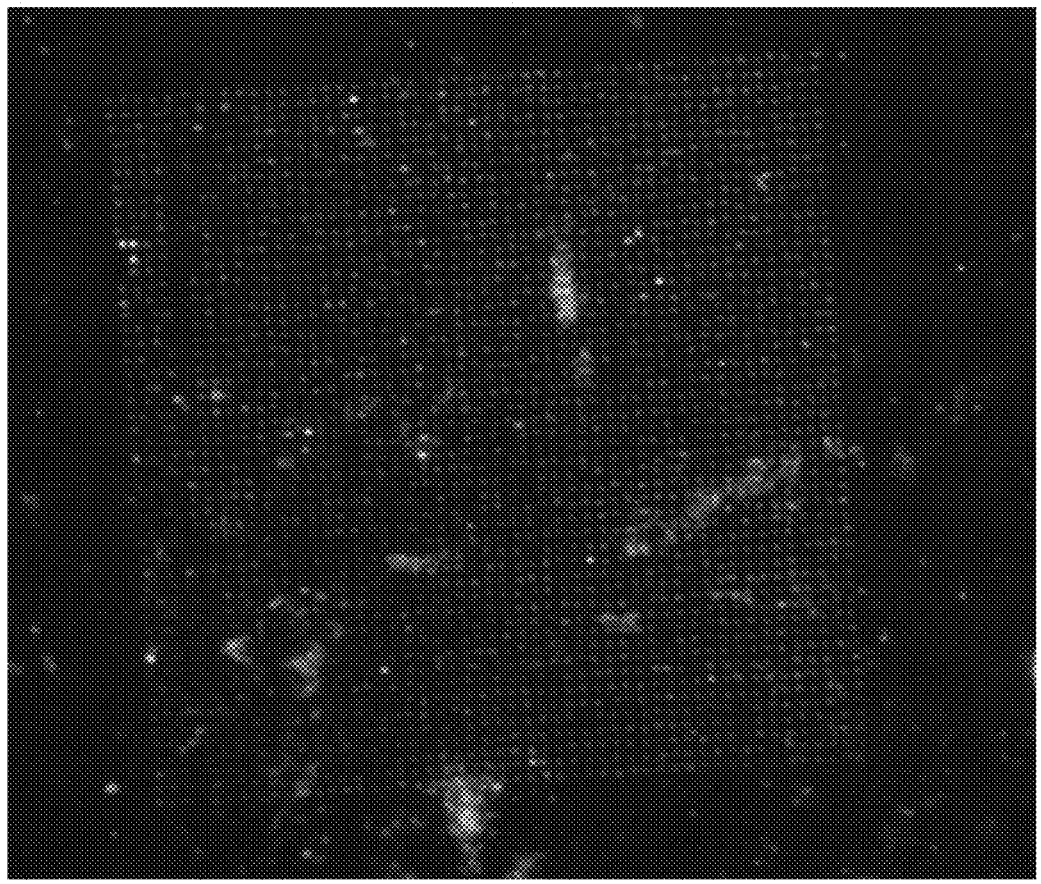
FIG. 8 depicts the clonal capture of one of two hyperbranched RCA amplicons to a grid of 200×200 nm spots with 1200 nm spacing. Two separate tubes of amplicons were generated, one using Cy3 fluorescent primers and the other Cy5. Both tubes of amplicons used biotinylated primers, and the spots on the nanogrid were activated with streptavidin. 40× objective, NA=0.9, 5 second exposure.
Figure 9:
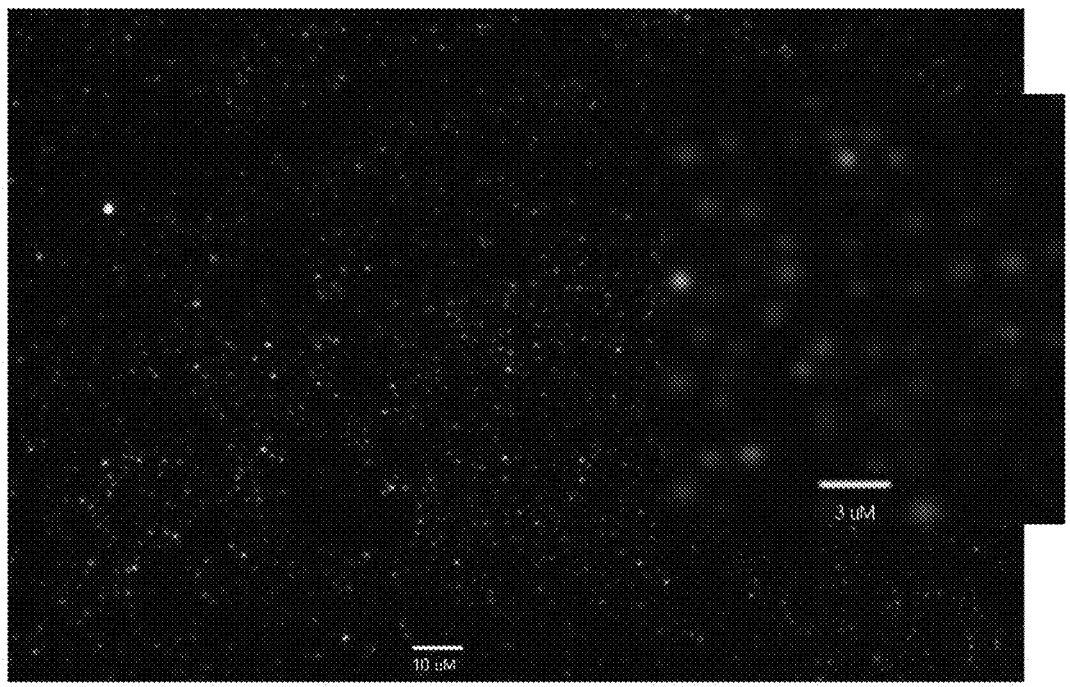
FIG. 9 depicts packing of linear RCA amplicons of approximately 8,000 base pair length so that they can still be differentially discerned yet they are of the density desired for the nanogrids. The image is false colored to depict the hybridization of Cy3 and Cy5 detection oligomers. The rolonies were aligned through a third image taken with a FITC labeled universal primer. Objective 40×, NA 0.9.
Figure 10:
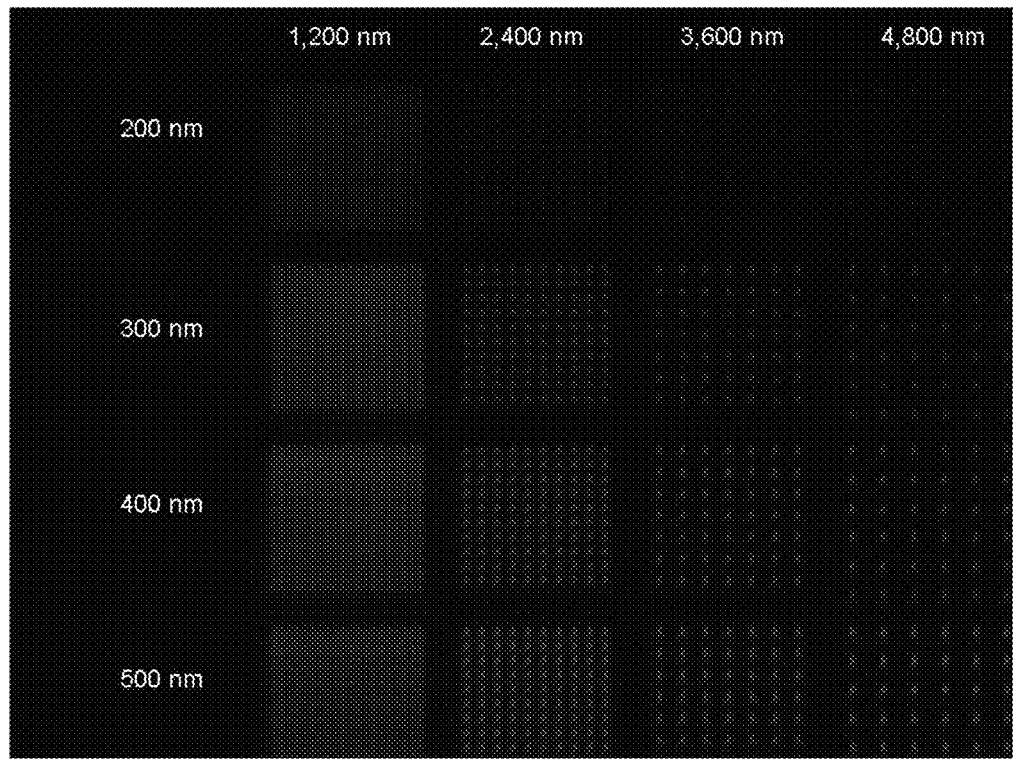
FIG. 10 depicts a combinatorial grid pattern used to interrogate optimal spot size and spacing for the nanogrids. The left hand axis describes the spot sizes and the top axis describes the spot spacing.
Figure 11:
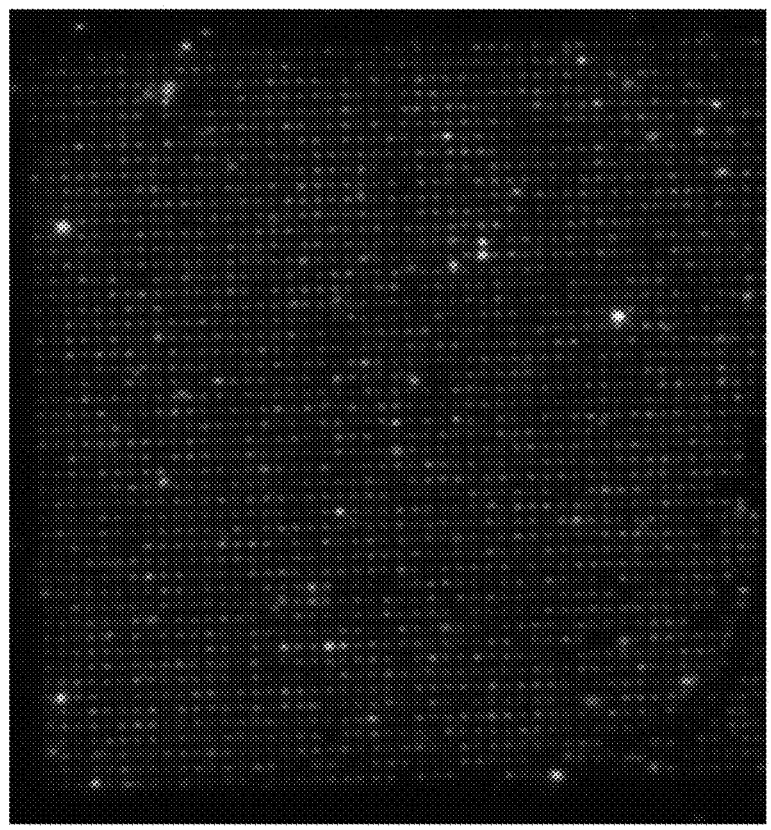
FIG. 11 depicts the capture of two different species of linear RCA amplicons to the nanogrid through hybridization to surface-spot bound primers. These primers captured the concatemers through hybridization to the concatemers every 90 base pairs. Concatemers were detected through hybridization with Cy3 and Cy5 labeled oligomers, and was false colored. Alignment of the two images was aided with a universal FITC detection oligomer. 40×, NA 0.9.
Figure 12:
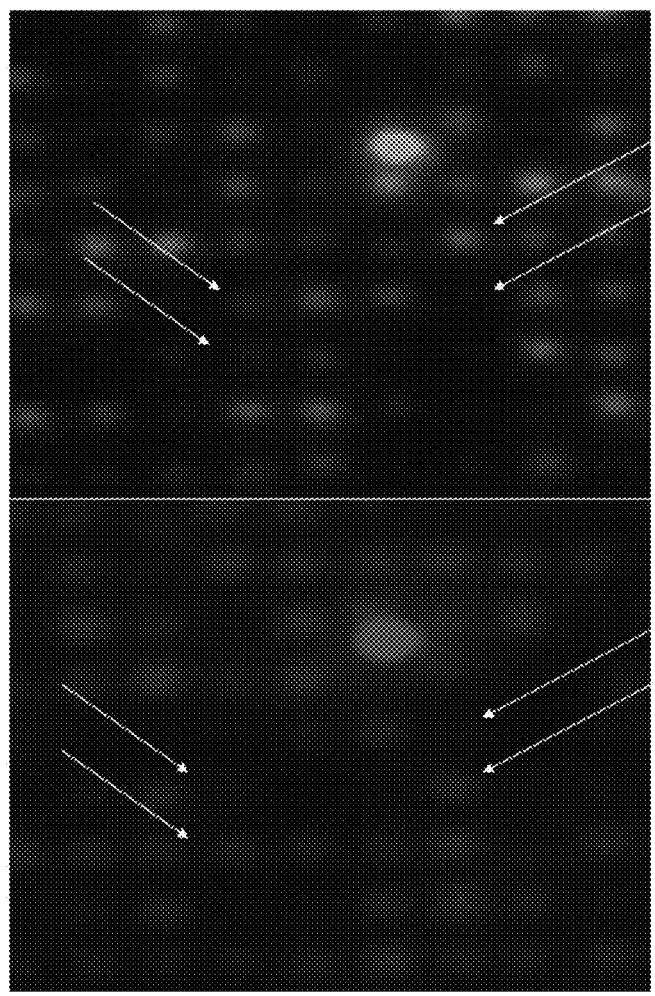
FIG. 12 depicts the issue of clonality in FIG. 11. A subset of the spots contain only one color, indicating that they have captured only one amplicon, while others have captured more than one.
Figure 13:
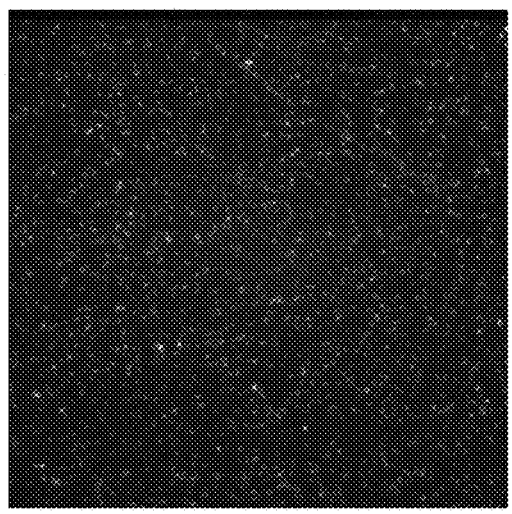
FIG. 13 depicts sequencing by ligation (SBL) of a synthetic library with 8 random bases flanked by the primer sequences FISSEQ-F and FISSEQ-R. The universal primer was first hybridized, imaged and then stripped with 95° C. dH$_2$O. After detection of the first base, the detection oligomers were stripped with 95° C. dH$_2$O and the fifth base was queried. The image was obtained with 20× objective, NA 0.75 with a 1.5× relay lens.
Figure 13:
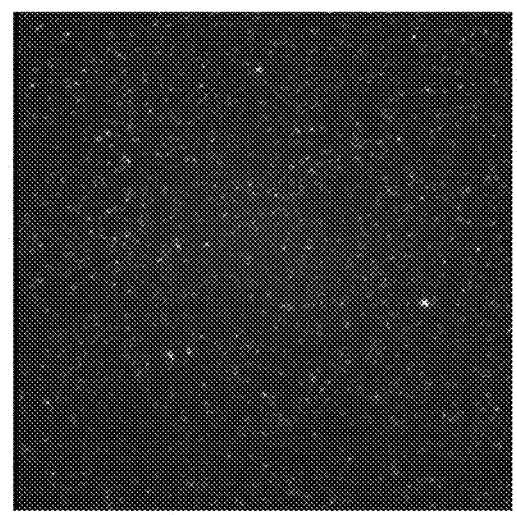
Figure 14:
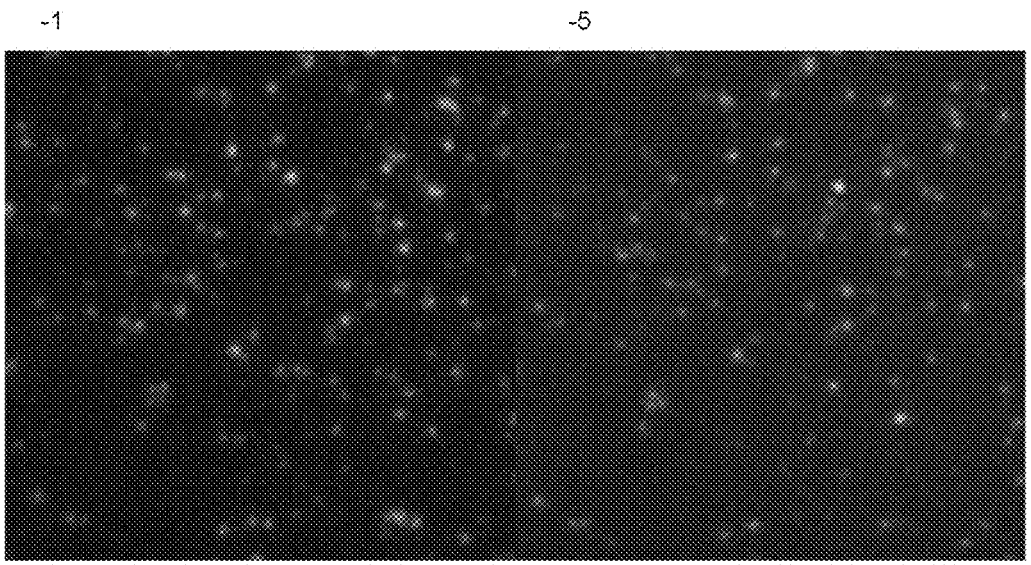
FIG. 14 depicts a detail from FIG. 13. In the left image, there were only two possibilities, Cy3 (green) and Cy5 (red). In the right image, all four bases were present, but only the Cy3 and Cy5 images are shown.

In one exemplary embodiment, sequencing by ligation was performed on linear RCA amplicons irreversibly bound to the surface of a slide (FIGS. 13 and 14). In one experiment, the clonal binding of concatemers to the spots occurred at low frequency of occupation (FIG. 8), and in another (using a different technique) 100% occupancy of spots was achieved, but with clonality (FIGS. 11 and 12). Hybridization of fluorescently labeled oligomers has confirmed that the concatemers can be clonally packed with a density approaching the near-term desired density of one spot per 1.44 microns$^2$ (FIG. 9). The combinatorial nanogrids were generated to assess various spot sizes and spacing (FIG. 10).

In certain experiments, single-stranded DNA was able to irreversibly bind the slide surface despite the lack of binding media such biotin or amine groups. Without intending to be bound by scientific theory, this may have been due to static interaction, van der Waals forces, and/or the exocyclic amines on the DNA, alone or in combination with the active binding group(s). Steric occlusion can be used to maximally pack an amine-reactive slide with ssDNA concatemers.

In certain exemplary aspects, (1) modifications of the passivated surface on the nanogrid, (2) increases of the stringency of the detergent present in the nanospot-concatemer binding buffer, and (3) modifications of the DNA concatemer to make it less prone to non-specific binding can be performed.

Regarding aspect two above, building a second strand for the ssDNA concatemer having a good binding group is one simple way to make it less reactive. A unique terminal primer can then be attached (or used to prime the polymerization of the second strand) which can be used to hybridize in one place to the surface primer, or terminal transferase can be used to attach a chain of biotinylated or aminated dNTPs. The terminal transferase can also be used to add 300-500 repeats of a single dNTP, such as dTTP which can hybridize to a poly-A tail on the surface of the spot. Invitrogen (Carlsbad, Calif.) produces a Kilobase Binder buffer which aids in the binding of 10 kb DNA strands with a single biotin to streptavidin coated beads. This would be a new application for this buffer.

In other exemplary embodiments, the tightness of the amplicons once they are surface bound will be increased. 50 minute RCA reactions have created concatemers that occupied between 12 and 17 pixels on the surface when bound non-specifically. Attaching the DNA at only the end could allow for greater packing as well as shorter concatemers. Another exemplary approach is to use amine modified dNTPs in the creation of the original concatemer and using a bifunctional amine binding chemical (e.g., 1,4-phenylene-disiothiocyanate (PDC), bis(sulfosuccinimidyl) suberate (BS3) or the like) to collapse the concatemer upon itself. Yet another exemplary approach would be to use the DNA staples currently used for DNA origami to hybridize to two different portions of the concatemer and fold it upon itself.

EXAMPLE XIV

Sequencing by Ligation on Linear RCA Amplicons

Φ29 Mediated RCA Reaction

TABLE 3

| Reagent | Concentration | μL | Amount |
| --- | --- | --- | --- |
| Template | 1 μM | 2.5 | 2.5 pmol |
| Primer | 10 μM | 1 | 10 pmol |
| dNTP | 25 mM | 0.2 | 0.2 μmol |
| RepliPhi | 10X | 5 | 1X |
| Phi29 | 1000 Units | 0.3 | 300 units |
| DTT | 100 mM | 4.0 | 2X |
| dH2O | | 37.0 | |

Amine or biotin modified primers were used. Before addition of the polymerase, the sample was pre-heated to 95° C. for 3 minutes and then at the $T_m$ of the primer for 5 minutes. The polymerase was added after cooling to 30° C. and then allowed to react for approximately 50 minutes (polymerase added at 2240 base pairs/minute). Inactivation was performed by a 20 minute incubation at 65° C.

AminoSilane Treatment of Glass
1. Clean glass was used.
2. The glass was incubated at room temperature for 30 minutes in 0.5% aminopropyltriethoxysilane in acidic methanol (95:5 Methanol:0.1 mM Acetic Acid) to add multiple layers of aminopropyl groups along the entire SO$_2$ surface. Washed clean with Acetone/Methanol as needed ensuring that there was no visible spotting.
3. The glass was placed on a hotplate at approximately 120° C. for one minute to help solidify the aminosilane layer and break any bonds that were not connected to the bottom SO$_2$ surface.
4. The glass was placed in water for a few seconds to remove any aminosilane that was not attached to the glass surface.
5. The glass was dried, and a very stable aminosilane monolayer was obtained.

PDC Treatment of AminoSilanized Glass
1. Aminosilanized glass was used.
2. The glass was washed with acetone and dried using heat or compressed air.
3. The glass was incubated at room temperature for 30 minutes in 0.5% phenylene diisothiocyanate (PDC) dissolved in 1:9 solution (v:v) of pyridine:anhydrous N,N-dimethylformamide (DMF).
4. The glass was washed with methanol and acetone.
5. The glass was stored in a dessicator until use.

Alternative Amine-Reactive Slides
1. Clean glass was used.
2. The glass was incubated at room temperature in 2% 3-glycidoxytrimethoxysilane in acetone (v:v) for at least 30 minutes.
3. The glass was removed and washed once with acetone immediately before removal.

Ligation Sequencing (Offline)

Minus Side: leading off of FISSEQ-F complement and the anchor was phosphorylated.

Plus Side: leading off of FISSEQ-R and the nonamer was phosphorylated.

Stripping Reaction

50 μL 0.1 M NaOH

Incubated ten minutes at room temperature and then washed.

Hybridization Reaction

50 μL 6×SSPE with 0.01% Triton-X-100

0.5 μL 1 mM Anchor Primer

Incubated five minutes at 56° C. followed by two minutes at 42° C. and washed.

Ligation Reaction

40 μL dH2O

5 μL 10× T4 Ligation Buffer

4 μL Appropriate Nonamer Mix (10 μM)

1 μL High Concentration DNA Ligase

Incubated for thirty minutes at 35° C. and washed.

ssDNA Concatemer Binding

Template DNA (no need to purify from RepliPhi Buffer) and 25 mg/ml sodium bicarbonate buffer (pH 9.0) with 0.01% Triton X-100 were mixed and allowed to bind for 60 minutes in a humidity chamber at room temperature.

What is claimed:

1. A method of sequencing a polynucleotide immobilized on an array comprising:
    synthesizing a concatemer of a polynucleotide by rolling circle amplification;
    immobilizing the concatemer to the array, wherein the array comprises a substrate having a plurality of specific functionalized regions attached to the substrate in a pattern forming an ordered array, wherein each specific functionalized region comprises an inner spot functionalized with a first group which serves to capture the concatemer and an outer spot functionalized with a second group which serves as an attachment point for an amplification primer, wherein the concatermer is immobilized to the inner spot, and wherein the concatemer has a cross-sectional diameter greater than the diameter of the inner spot; and
    sequencing the immobilized concatemer.

2. The method of claim 1, wherein the concatemer has a cross-sectional diameter of at least 200 nanometers.

3. The method of claim 1, wherein the concatemer has a cross-sectional diameter of at least 300 nanometers.

4. The method of claim 1, wherein the polynucleotide is DNA.

5. The method of claim 1, wherein one concatemer is immobilized at the plurality of specific functionalized regions.

6. The method of claim 1, wherein the array has at least 100 specific functionalized regions.

7. The method of claim 6, wherein one concatemer is immobilized at each of the plurality of specific functionalized regions.

8. The method of claim 6, wherein at least 90 of the specific functionalized regions each contains one immobilized concatemer.

9. The method of claim 1, wherein the array has at least 1000 specific functionalized regions.

10. The method of claim 1, wherein the array has at least 10,000 specific functionalized regions.

11. The method of claim 1, wherein sequencing the immobilized concatemer is performed by fluorescent in situ sequencing.

12. The method of claim 1, wherein the array is a nanoarray.

13. The method of claim 1, wherein optical magnification is used to sequence the immobilized concatemer.

14. The method of claim 1, wherein immobilization is performed by hybridization.

15. The method of claim 1, wherein immobilization is performed by an interaction selected from the group consisting of biotin-avidin capture, biotin-streptavidin capture, NHS-ester capture, thioether linkage, static charge interactions and van der Waals forces.

16. A method of sequencing a polynucleotide immobilized on an comprising:
    synthesizing a concatemer of a polynucleotide by rolling circle amplification
    immobilizing the concatemer to the array, wherein the array comprises a substrate having a plurality of specific functionalized regions attached to the substrate in a pattern forming an ordered array, wherein each specific functionalized region comprises an inner spot functionalized with a first group which serves to capture the concatemer and an outer spot functionalized with a second group which serves as an attachment point for an amplification primer, wherein the concatermer is immobilized to the inner spot, and wherein the concatemer has a cross-sectional diameter greater than the diameter of the inner spot;
    clonally amplifying the immobilized concatemer to make a clonally amplified concatemer; and
    sequencing the clonally amplified concatemer.

17. The method of claim 16, wherein clonally amplifying is performed by a method selected from the group consisting of rolling circle amplification, multiple displacement amplification, thermophilic helicase-dependent amplification and bridge PCR.

18. The method of claim 17, wherein rolling circle amplification is selected from the group consisting of hyperbranched rolling circle amplification, padlock probe rolling circle amplification and linear rolling circle amplification.

19. The method of claim 1, wherein immobilization is performed by biotin-avidin capture or NHS-ester capture.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
tcagaactca cctgttagac                                                   20

<210> SEQ ID NO 2
<211> LENGTH: 48
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 23, 24, 25, 26, 27, 28,
      29, 30, 31, 32
<223> OTHER INFORMATION: n = A,T,C or G

<400> SEQUENCE: 2
nnnnnnnnnn ttcttcttct tcnnnnnnnn nntcaagtca atcggtcc                    48

<210> SEQ ID NO 3
<211> LENGTH: 48
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 14, 17, 20, 23, 24,
      25, 26, 27, 28, 29, 30, 31, 32
<223> OTHER INFORMATION: n = A,T,C or G

<400> SEQUENCE: 3
nnnnnnnnnn ntcntcntcn tcnnnnnnnn nntcaagtca atcggtcc                    48

<210> SEQ ID NO 4
<211> LENGTH: 45
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 20, 21, 22, 23, 24, 25,
```

```
         26, 27, 28, 29
<223> OTHER INFORMATION: n = A,T,C or G

<400> SEQUENCE: 4
nnnnnnnnnn ttcttcttcn nnnnnnnnnt caagtcaatc ggtcc            45

<210> SEQ ID NO 5
<211> LENGTH: 45
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 14, 17, 20, 21, 22,
         23, 24, 25, 26, 27, 28, 29
<223> OTHER INFORMATION: n = A,T,C or G

<400> SEQUENCE: 5
nnnnnnnnnn ntcntcntcn nnnnnnnnnt caagtcaatc ggtcc            45

<210> SEQ ID NO 6
<211> LENGTH: 42
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 17, 18, 19, 20, 21, 22,
         23, 24, 25, 26
<223> OTHER INFORMATION: n = A,T,C or G

<400> SEQUENCE: 6
nnnnnnnnnn ttcttcnnnn nnnnnntcaa gtcaatcggt cc              42

<210> SEQ ID NO 7
<211> LENGTH: 42
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 14, 17, 18, 19, 20,
         21, 22, 23, 24, 25, 26
<223> OTHER INFORMATION: n = A,T,C or G

<400> SEQUENCE: 7
nnnnnnnnnn ntcntcnnnn nnnnnntcaa gtcaatcggt cc              42

<210> SEQ ID NO 8
<211> LENGTH: 42
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 17, 18, 19, 20, 21, 22,
         23, 24, 25, 26
<223> OTHER INFORMATION: n = A,T,C or G

<400> SEQUENCE: 8
nnnnnnnnnn ctcatcnnnn nnnnnntcaa gtcaatcggt cc              42

<210> SEQ ID NO 9
<211> LENGTH: 48
<212> TYPE: DNA
```

<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 23, 24, 25, 26, 27, 28,
    29, 30, 31, 32
<223> OTHER INFORMATION: n = A,T,C or G

<400> SEQUENCE: 9
nnnnnnnnnn ctcatcctca tcnnnnnnnn nntcaagtca atcggtcc         48

<210> SEQ ID NO 10
<211> LENGTH: 47
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 21, 22, 23, 24, 25, 26,
    27, 28, 29, 30, 31
<223> OTHER INFORMATION: n = A,T,C or G

<400> SEQUENCE: 10
nnnnnnnnnn wtttgccacc nnnnnnnnnnn ntcaagtcaa tcggtcc         47

<210> SEQ ID NO 11
<211> LENGTH: 47
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 12, 13, 22, 23, 24,
    25, 26, 27, 28, 29, 30, 31
<223> OTHER INFORMATION: n = A,T,C or G

<400> SEQUENCE: 11
nnnnnnnnnn nnnyccrcy rnnnnnnnnn ntcaagtcaa tcggtcc           47

<210> SEQ ID NO 12
<211> LENGTH: 47
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 12, 13, 21, 22, 23,
    24, 25, 26, 27, 28, 29, 30, 31
<223> OTHER INFORMATION: n = A,T,C or G

<400> SEQUENCE: 12
nnnnnnnnnn nnncgccacc nnnnnnnnnn ntcaagtcaa tcggtcc          47

<210> SEQ ID NO 13
<211> LENGTH: 48
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 11, 12, 13, 14, 15, 16,
    17, 18, 19, 20, 21, 22, 23, 24, 25, 26, 27, 28, 29, 30
<223> OTHER INFORMATION: n = A,T,C or G
<220> FEATURE:
<221> NAME/KEY: misc_feature
<222> LOCATION: 31, 32

<223> OTHER INFORMATION: n = A,T,C or G

<400> SEQUENCE: 13
nnnnnnnnnn nnnnnnnnnn nnnnnnnnnn nntcaagtca atcggtcc                48

<210> SEQ ID NO 14
<211> LENGTH: 48
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 23, 24, 25, 26, 27, 28,
      29, 30, 31, 32
<223> OTHER INFORMATION: n = A,T,C or G

<400> SEQUENCE: 14
nnnnnnnnnn tgtcctactg ctnnnnnnnn nntcaagtca atcggtcc                48

<210> SEQ ID NO 15
<211> LENGTH: 48
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 23, 24, 25, 26, 27, 28,
      29, 30, 31, 32
<223> OTHER INFORMATION: n = A,T,C or G

<400> SEQUENCE: 15
nnnnnnnnnn yyyyyyyyyy yynnnnnnnn nntcaagtca atcggtcc                48

<210> SEQ ID NO 16
<211> LENGTH: 45
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 20, 21, 22, 23, 24, 25,
      26, 27, 28, 29
<223> OTHER INFORMATION: n = A,T,C or G

<400> SEQUENCE: 16
nnnnnnnnnn yyyyyyyyyn nnnnnnnnnt caagtcaatc ggtcc                   45

<210> SEQ ID NO 17
<211> LENGTH: 42
<212> TYPE: DNA
<213> ORGANISM: Artificial Sequence
<220> FEATURE:
<223> OTHER INFORMATION: control oligonucleotide
<220> FEATURE:
<221> NAME/KEY: misc_feature
<222> LOCATION: 1, 2, 3, 4, 5, 6, 7, 8, 9, 10, 17, 18, 19, 20, 21, 22,
      23, 24, 25, 26
<223> OTHER INFORMATION: n = A,T,C or G

<400> SEQUENCE: 17
nnnnnnnnnn yyyyyynnnn nnnnnntcaa gtcaatcggt cc                      42

<210> SEQ ID NO 18
<211> LENGTH: 16
<212> TYPE: DNA
<213> ORGANISM: Artificial Sequence

```
<220> FEATURE:
<223> OTHER INFORMATION: universal primer

<400> SEQUENCE: 18
ggaccgattg acttga                                              16

<210> SEQ ID NO 19
<211> LENGTH: 45
<212> TYPE: DNA
<213> ORGANISM: Artificial Sequence
<220> FEATURE:
<223> OTHER INFORMATION: positive control oligonucleotide for Rap1
      binding site

<400> SEQUENCE: 19
actttcacta aatacaccca tacacaccaa tcttggattc tactc               45

<210> SEQ ID NO 20
<211> LENGTH: 45
<212> TYPE: DNA
<213> ORGANISM: Artificial Sequence
<220> FEATURE:
<223> OTHER INFORMATION: positive control oligonucleotide for Rap1
      binding site

<400> SEQUENCE: 20
gagtagaatc caagattggt gtgtatgggt gtatttagtg aaagt               45

<210> SEQ ID NO 21
<211> LENGTH: 45
<212> TYPE: DNA
<213> ORGANISM: Artificial Sequence
<220> FEATURE:
<223> OTHER INFORMATION: negative control oligonucleotide for Rap1
      binding site

<400> SEQUENCE: 21
tccgtatgtt tatgttgcta ttttgatgta aataaaaaag ttgaa               45

<210> SEQ ID NO 22
<211> LENGTH: 45
<212> TYPE: DNA
<213> ORGANISM: Artificial Sequence
<220> FEATURE:
<223> OTHER INFORMATION: negative control oligonucleotide for Rap1
      binding site

<400> SEQUENCE: 22
ttcaactttt ttatttacat caaaatagca acataaacat acgga               45

<210> SEQ ID NO 23
<211> LENGTH: 45
<212> TYPE: DNA
<213> ORGANISM: Artificial Sequence
<220> FEATURE:
<223> OTHER INFORMATION: probe

<400> SEQUENCE: 23
aaacaatgcc cactagccgg ggtgtacggg accttaaatc taagt               45

<210> SEQ ID NO 24
<211> LENGTH: 45
<212> TYPE: DNA
<213> ORGANISM: Artificial Sequence
<220> FEATURE:
<223> OTHER INFORMATION: probe
```

```
<400> SEQUENCE: 24
acttagattt aaggtcccgt acacccoggc tagtgggcat tgttt                45

<210> SEQ ID NO 25
<211> LENGTH: 45
<212> TYPE: DNA
<213> ORGANISM: Artificial Sequence
<220> FEATURE:
<223> OTHER INFORMATION: probe

<400> SEQUENCE: 25
gggcatactt tacggggtgc acggatttta gcagtctttt tcttt                45

<210> SEQ ID NO 26
<211> LENGTH: 45
<212> TYPE: DNA
<213> ORGANISM: Artificial Sequence
<220> FEATURE:
<223> OTHER INFORMATION: probe

<400> SEQUENCE: 26
aaagaaaaag actgctaaaa tccgtgcacc ccgtaaagta tgccc                45
```